(12) United States Patent
Wei

(10) Patent No.: US 8,359,090 B2
(45) Date of Patent: Jan. 22, 2013

(54) ELECTROCARDIOGRAPH WITH EXTENDED LEAD FUNCTION, AND EXTENDED LEAD ELECTROCARDIOGRAM DERIVING METHOD

(75) Inventor: Daming Wei, Aizuwakamatsu (JP)

(73) Assignees: Daming Wei; Nihon Kohden Corporation (JP)

( * ) Notice: Subject to any disclaimer, the term of this patent is extended or adjusted under 35 U.S.C. 154(b) by 0 days.

(21) Appl. No.: 13/193,129

(22) Filed: Jul. 28, 2011

(65) Prior Publication Data

US 2011/0288426 A1 Nov. 24, 2011

Related U.S. Application Data

(62) Division of application No. 12/826,065, filed on Jun. 29, 2010, now Pat. No. 8,005,532, which is a division of application No. 10/546,785, filed as application No. PCT/JP2004/002251 on Feb. 26, 2004, now abandoned.

(30) Foreign Application Priority Data

Feb. 26, 2003 (JP) ................................ 2003-048780
Nov. 14, 2003 (JP) ................................ 2003-385497

(51) Int. Cl.
*A61B 5/0402* (2006.01)

(52) U.S. Cl. ...................................................... 600/509
(58) Field of Classification Search .................. 600/512, 600/509
See application file for complete search history.

(56) References Cited

U.S. PATENT DOCUMENTS

| 4,850,370 | A | 7/1989 | Dower |
| 5,058,598 | A | 10/1991 | Nicklas et al. |
| 5,711,304 | A | * | 1/1998 | Dower .......................... 600/523 |
| 6,119,035 | A | 9/2000 | Wang |
| 6,643,539 | B2 | 11/2003 | Meij et al. |
| 6,690,967 | B2 | 2/2004 | Meij et al. |
| 2002/0035334 | A1* | 3/2002 | Meij et al. ..................... 600/509 |
| 2002/0045837 | A1 | 4/2002 | Wei et al. |

(Continued)

FOREIGN PATENT DOCUMENTS

JP 7-95968 4/1995

(Continued)

OTHER PUBLICATIONS

Shunka Nakamura, "Holter Shindenzuho ni Okeru Yudosu Seiyaku heno Ichishian", Japanese Journal of electrocardiology, "Shindenzu", Japanese Journal of electrocardiology, Jul. 31, 1989, vol. 9, No. 4, pp. 446-455.

(Continued)

*Primary Examiner* — George Evanisko
(74) *Attorney, Agent, or Firm* — Ostrolenk Faber LLP

(57) ABSTRACT

There are provided an electrocardiograph with an extended lead function and an extended lead ECG deriving method capable of easily deriving an ECG signal of an extended lead ECG by an arithmetic operation, based on ECG signals of a standard 12-lead ECG measured by a potential detector 10. An ECG memory 12 stores the ECG signals measured as the standard 12-lead ECG by the potential detector 10. An extended lead ECG calculator 16 calculates extended lead ECGs V7-V9 from the ECG signals stored in the ECG memory 12, using coefficients α representing a relationship among leads. The extended lead ECGs V7-V9 calculated are displayed through an extended lead ECG waveform outputting device 18 on a display monitor 20.

7 Claims, 18 Drawing Sheets

U.S. PATENT DOCUMENTS

2003/0216655 A1  11/2003  Schreck

FOREIGN PATENT DOCUMENTS

| | | |
|---|---|---|
| JP | 2002-34943 A | 2/2002 |
| JP | 2002-282229 | 10/2002 |
| JP | 2002-282230 | 10/2002 |
| JP | 2006-141813 | 6/2006 |
| WO | WO 02/11615 A2 | 2/2002 |

OTHER PUBLICATIONS

English translation of International Preliminary Report on Patentability issued for the PCT application issued Mar. 2, 2006.
Office Action issued Jun. 5, 2007 in corresponding Japanese Patent Application No. 2005-502917.
Office Action issued Sep. 4, 2007 in corresponding Japanese Patent Application No. 2005-502917.
International Search Report issued May 11, 2004.
Notice of Allowance issued Jun. 24, 2008 in counterpart Japanese Patent Application.
Search Report issued on May 15, 2008 in counterpart European application.
Daming Wei "Deriving the 12-lead electrocardiogram from four standard leads based on the Frank torso model", Engineering in Medicine and Biology Society, 2001, Proceedings of 23rd Annual International Conference of IEEE, 2001; vol. 1, p. 381-384.
Daming Wei "Derived electrocardiograms on the posterior leads from 12-lead system: method and evaluation", Engineering in Medicine and Biology Society, 2003, Proceedings of 25th Annual International Conference of IEEE, Sep. 17-21, 2003; vol. 1, p. 74-77.
Daming Wei "Deriving the 12-lead Electrocardiogram from four standard leads using information redundancy in the 12-lead system", International Journal of Bioelectromagnetism, 2002; vol. 4, No. 2, p. 127-128.
Schreck et al. "Derivation of the 12-lead electrocardiogram using abstract factor analysis and simplex optimization", International Journal of Bioelectromagnetism, 2002; vol. 4, No. 2, p. 337-338.

* cited by examiner ical application No. PCT/JP2004/002251 filed 26 Feb.
ELECTROCARDIOGRAPH WITH EXTENDED LEAD FUNCTION, AND EXTENDED LEAD ELECTROCARDIOGRAM DERIVING METHOD

CROSS-REFERENCE TO RELATED APPLICATIONS

The present application is a Divisional application of U.S. Ser. No. 12/826,065, filed Jun. 29, 2010, which is a divisional application of U.S. Ser. No. 10/546,785 filed May 24, 2006, which is a 35 U.S.C. §371 national phase conversion of International Application No. PCT/JP2004/002251 filed 26 Feb. 2004, which claims priority from Japanese Patent application No. 2003-048780 filed 26 Feb. 2003 and Japanese Patent Application 2003-385497 filed 14 Nov. 2003; all being incorporated herein by reference.

TECHNICAL FIELD

The present invention relates to an electrocardiograph with an extended lead function and an extended lead electrocardiogram (ECG) deriving method capable of easily and correctly obtaining through an arithmetic operation, an extended lead ECG effective to diagnoses of an ischemic heart disease, an acute cardiac infarction, etc. in the cardiac muscle regions difficult to diagnose even with the standard 12-lead ECG.

BACKGROUND ART

For measuring an ECG of a patient, ten electrodes connected to an electrocardiograph are used as mounted at six locations for measurement of chest leads and at four locations for measurement of limb leads. Then the electrocardiograph calculates and outputs the six limb lead waveforms (I, II, III, aVR, aVL, and aVF) of the standard 12 leads and the six chest lead waveforms (V1, V2, V3, V4, V5, and V6) of the standard 12 leads, based on heart potentials detected from these ten electrodes.

In general, the relationship based on that the standard 12-lead ECG is obtained is given as described in [Table 1] below.

TABLE 1

Lead I: vL − vR
Lead II: vF − vR
Lead III: vF − vL
Lead aVR: vR − (vL + vF)/2
Lead aVL: vL − (vR + vF)/2
Lead aVF: vF − (vL + vR)/2
Lead V1: v1 − (vR + vL + vF)/3
Lead V2: v2 − (vR + vL + vF)/3
Lead V3: v3 − (vR + vL + vF)/3
Lead V4: v4 − (vR + vL + vF)/3
Lead V5: v5 − (vR + vL + vF)/3
Lead V6: v6 − (vR + vL + vF)/3

In the above relationship, each v represents a potential detected at the electrode-mounted position.

The diagnosis of a patient's heart disease with a number of electrodes as described above can be performed in rest state in a bed of the patient as long as it is done within a fully-equipped hospital or the like.

However, for example, in cases of home and emergency medical cares, it is often the case that there is no extra room for use of many electrodes and attachment of each electrode at the appropriate position on the body surface of the living body in view of the patient's condition. Furthermore, it is sometimes difficult to transmit signals of multiple channels for acquisition of many lead waveforms. In such cases, only one channel (one lead) is commonly used to transmit the ECG signals, and the diagnosis of the heart disease is made by using at most two to four electrodes to measure some lead waveforms out of the standard 12-lead waveforms.

Under such circumstances, the inventor has developed a construction method of a standard 12-lead ECG and an ECG inspection apparatus for reconstructing the standard 12-lead ECG permitting appropriate diagnoses and treatment of various heart diseases, based on a subset of a lead system consisting of a minimum number of leads for acquisition of the conventionally known standard 12-lead ECG, and filed a patent application (cf. Patent Document 1).

Specifically, the construction method of the standard 12-lead ECG described in the above Patent Document 1 uses as the subset of the lead system consisting of the minimum number of channels, Leads I and II of the limb leads, and two leads of the chest leads, Lead V1 and, Lead V5 or Lead V6, for acquisition of the standard 12-lead ECG. Using these leads, Lead III and Leads aV (Lead aVR, Lead aVL, and Lead aVF) can be determined by an arithmetic operation based on the characteristic relationship among the leads presented in Table 1. The remaining leads of the chest leads, Lead V2, Lead V3, Lead V4, and, Lead V6 or Lead V5, can be determined by an arithmetic operation from the relationship among potentials, lead vectors, and a heart vector.

Since the standard 12-lead ECG obtained in this manner uses the subset of the lead system of the conventional standard 12-lead ECG each electrode can be mounted as readily and accurately positioned at each predetermined location and this work does not require much skill. In addition, the standard 12-lead ECG can be reconstructed with high precision, so that the diagnoses and treatment can be appropriately performed for the various heart diseases.

However, not only in the case where the standard 12-lead ECG is obtained from the six limb leads and six chest leads with the ten electrodes as before, but also in the case where the highly accurate standard 12-lead ECG is obtained by the method described in Patent Document 1 as above, it is relatively easy to confirm and diagnose an anomaly in the ECG waveforms, for example, if an occlusion of the coronary artery feeding blood to the heart muscle among the cardiac infarctions occurs in the anterior wall, the lateral wall, or the inferior wall of the heart muscle. On the contrary, if an occlusion of the coronary artery occurs at the posterior wall of the heart muscle, the electrode mounted locations are far from the posterior wall and the sensitivity of the ECG waveforms is thus too low to reflect the effect of the occlusion of the coronary artery on the ECG waveforms. In addition, the sensitivity to the right lateral wall of the heart muscle is also low because most of the electrode mounted positions of the standard 12-lead ECG are on the left side of the body surface. For this reason, it is highly likely that the occlusion of the coronary artery at the posterior wall, the right lateral wall, or the right inferior wall is overlooked in the diagnosis.

[Patent Document 1] Japanese Patent Application Laid-Open No. 2002-34943

It was thus conventionally common practice to obtain an extended lead ECG using Leads V7, V8, and V9 measured at electrode mounted locations on extensions of the chest leads and/or using Leads V3R, V4R, V5R, and V6R at electrode locations symmetric with the electrode locations of the chest leads, in order to make correct diagnoses of the aforementioned posterior myocardial infarction, pulmonary heart, pulmonary embolus, right ventricular infarction, right ventricular hypertrophy, dextrocardia, other stress-related right ventricular diseases, and so on. However, the electrode mounted positions for acquisition of the extended lead ECG of Leads V7, V8, and V9 are on the patient's back or the like. The patient needs to lie back in order to be kept at rest, whereas the patient is forced into an unnatural posture in order to mount the electrodes on the patient's back or the like. In addition, there also arises a problem that the electrode mounting operation is complicated. Moreover, the ordinary standard 12-lead electrocardiographs are unable to measure the extended lead ECG of Leads V7, V8, and V9 and Leads V3R, V4R, V5R, and V6R, and there arises a need for a special electrocardiograph with an extended lead ECG measuring function having the electrodes for measurement of the extended leads.

DISCLOSURE OF THE INVENTION

An object of the present invention is to solve the problems in the conventional technology as described above and to easily obtain an extended lead, without need for mounting an additional electrode other than the electrodes used for the 12 leads. Another object of the present invention is to easily obtain an extended lead, without need for mounting an electrode for the extended lead, from some of the leads of the 12-lead ECG.

The above objects of the present invention are achieved by providing an electrocardiograph with an extended lead function comprising a potential detector for measuring lead potentials of a 12-lead ECG or at least part of them; and extended lead potential calculating means for calculating an extended lead potential, based on the lead potentials of the 12-lead ECG or the part of the lead potentials measured by the potential detector.

In a preferred embodiment of the present invention, the extended lead potential calculating means uses a relationship among the measured lead potentials, a heart vector, and lead vectors to determine the heart vector on the basis of the lead potentials measured by the potential detector, and calculates the extended lead potential by use of the heart vector thus determined.

The extended lead potential calculating means may calculate the extended lead potential on the basis of the lead potentials measured by the potential detector, using transfer coefficients $\alpha$ representing a relationship among the leads.

The above objects of the present invention can also be achieved by performing an extended lead ECG deriving method comprising a first step of measuring at least part of lead potentials of a 12-lead ECG, and a second step of calculating an extended lead potential, based on the measured lead potentials out of the lead potentials of the 12-lead ECG.

In this extended lead ECG deriving method, preferably, the second step also comprises using a relationship among the lead potentials, a heart vector, and lead vectors to determine the heart vector on the basis of the measured lead potentials, and calculating the extended lead potential by use of the heart vector thus determined.

Alternatively, the second step may comprise calculating the extended lead potential on the basis of the measured lead potentials, using transfer coefficients $\alpha$ representing a relationship among the leads.

A method of deriving an extended lead ECG according to the present invention comprises performing an arithmetic operation to calculate a lead potential at an extended lead location except for a standard 12-lead ECG, based on ECG signals measured as standard lead potentials of the standard 12-lead ECG by a potential detector consisting of ten or less electrodes.

Another method of deriving an extended lead ECG according to the present invention comprises, based on ECG signals measured as standard lead potentials of a standard 12-lead ECG by a potential detector consisting of ten or less electrodes, determining a heart vector [H] on the basis of the measured ECG signals as the standard lead potentials of the standard 12-lead ECG from a relationship among the potentials [V], lead vectors [L], and the heart vector [H], and performing an arithmetic operation to calculate an extended lead potential of an extended lead ECG, using the heart vector [H] thus determined.

Still another method of deriving an extended lead ECG according to the present invention comprises storing ECG signals measured as standard lead potentials of a standard 12-lead ECG by a potential detector consisting of ten or less electrodes, performing an arithmetic operation to set transfer coefficients $\alpha$ for calculation of an extended lead potential on the basis of the standard lead potentials of the standard 12-lead ECG and extended lead potentials of the extended lead ECG measured in advance, and performing an arithmetic operation to calculate the extended lead potential of the extended lead ECG from the ECG signals measured as the standard lead potentials of the standard 12-lead ECG, using the transfer coefficients $\alpha$ set by the arithmetic operation.

Still another method of deriving an extended lead ECG according to the present invention comprises storing ECG signals measured as a standard 12-lead ECG by a potential detector, performing an arithmetic operation to set parameters for calculation of an extended lead ECG on the basis of lead potentials of the standard 12-lead ECG and lead potentials of the extended lead ECG measured in advance, and performing an arithmetic operation to calculate a lead potential of the extended lead ECG from the ECG signals measured as the standard 12-lead ECG, using the parameters set by the arithmetic operation.

Another electrocardiograph with an extended lead function according to the present invention comprises electrodes to be mounted on a body surface of a living body in order to obtain lead waveforms of a standard 12-ECG; a potential detector for measuring ECG signals of the standard 12-lead ECG from the respective electrodes; an ECG signal memory for storing each of the ECG signals of the standard 12-lead ECG measured by the potential detector; standard 12-lead ECG waveform means for performing waveform processing of the standard 12-lead ECG with input of the ECG signals obtained via the ECG signal memory; extended lead ECG signal calculating means for calculating an ECG signal of an extended lead ECG on the basis of calculation parameters $\alpha$ set in advance by an arithmetic operation with input of the ECG signals obtained via the ECG signal memory; extended lead ECG waveform outputting means for performing waveform processing of the extended lead ECG with input of the ECG signal calculated by the extended lead ECG signal calculating means; and a display monitor for simultaneously displaying on a screen, ECG waveform outputs from the standard 12-lead ECG waveform outputting means and from the extended lead ECG waveform outputting means.

The foregoing extended lead ECG preferably comprises some or all of Leads V7-V9, and Leads $V_{3R}$, $V_{4R}$, $V_{5R}$, and $V_{6R}$.

BEST MODE FOR CARRYING OUT THE INVENTION

Figure 1:
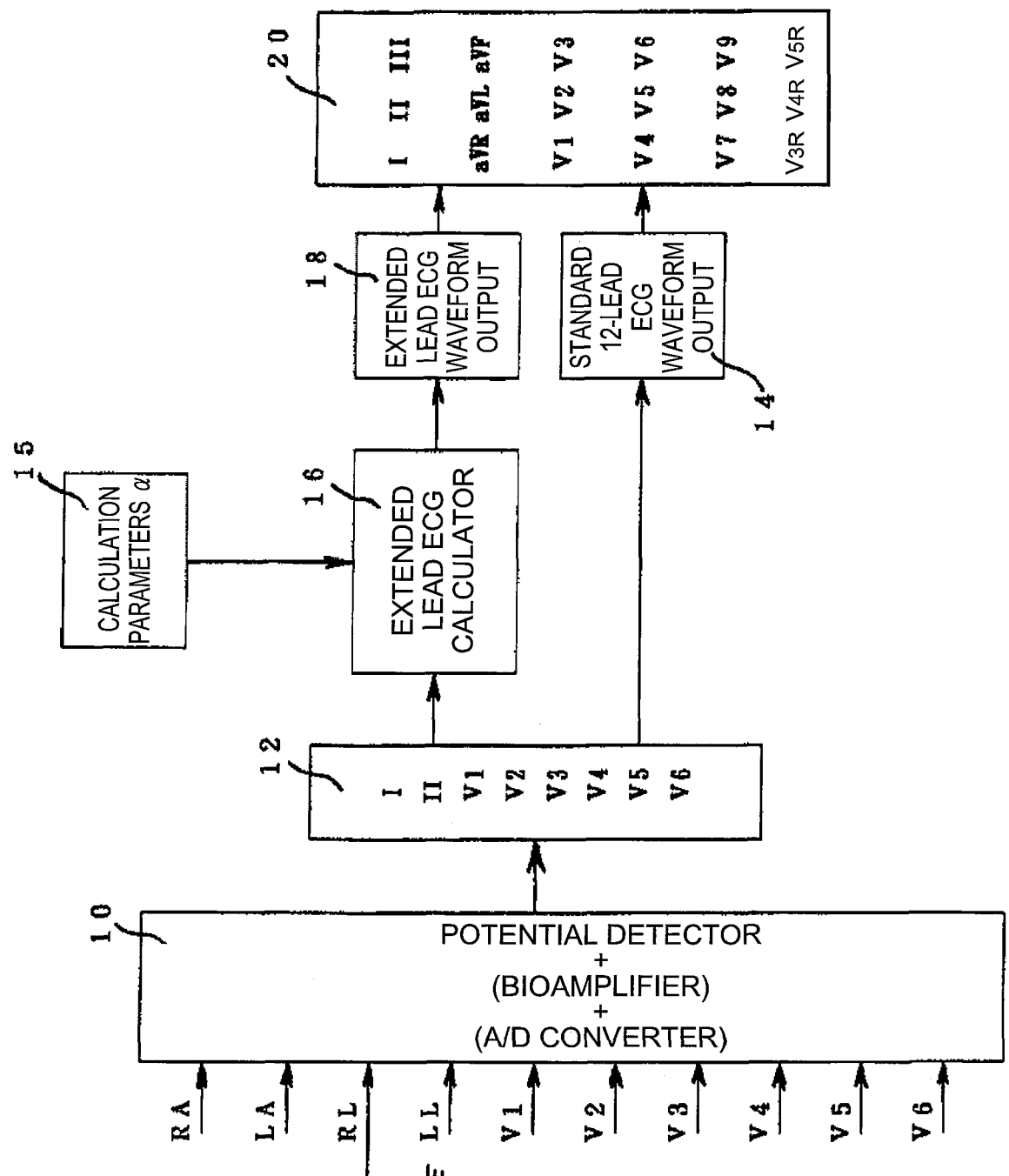
FIG. 1 is a system configuration diagram showing the first embodiment of the electrocardiograph according to the present invention.

The preferred embodiments of the present invention will be described below in detail with reference to the drawings.

First Embodiment

The first embodiment concerns a method and apparatus for making use of ECG signals measured at the electrode mounted locations of the standard 12-lead ECG by a potential detector of a standard 12-lead electrocardiograph, to perform an arithmetic operation to calculate, for example, extended leads including Leads V7, V8, and V9 at electrode mounted locations on extensions of the chest leads and Leads $V_{3R}$, $V_{4R}$, and $V_{5R}$.

Namely, the first embodiment is to calculate the extended leads V7, V8, V9 and $V_{3R}$, $V_{4R}$, $V_{5R}$, for example, from the eight ECG signals (I, II, V1, V2, V3, V4, V5, and V6) obtained by the standard 12-lead electrocardiograph, in order to calculate the heart potentials at the extended lead locations (ECG) from the ECG signals obtained by the potential detector of the 12-lead electrocardiograph.

(Principle of Method of Deriving Extended Lead ECG Using Lead Vectors)

In the clinical ECG, according to the lead theory, the cardiac source at an arbitrary time can be expressed by a Fixed Single Dipole and a potential (V) at an arbitrary lead location can be determined by Eqs (1-1) to (1-3) below.

$$V = L \cdot H \tag{1-1}$$

$$H = \begin{pmatrix} hx \\ hy \\ hz \end{pmatrix} \tag{1-2}$$

$$L = \begin{pmatrix} lx \\ ly \\ lz \end{pmatrix} \tag{1-3}$$

In the above equations, V represents a potential matrix, H the heart vector, and L a lead vector.

Therefore, the heart vector H varies depending upon the electric activity of the heart and the inner product of the heart vector H and the lead vector L provides a cardiac potential (ECG) V measured by the electrocardiograph. Since each lead vector L is defined by values inherent to a specific person, the cardiac potential can be determined by a spatial vector of electromotive force of the heart. Namely, a cardiac potential of an arbitrary lead can be determined by three parameters.

Accordingly, since the potential detector of the standard 12-lead electrocardiograph measures the eight ECG signals, it is possible to calculate an ECG potential at an arbitrary location on a body surface of a living body by use of these ECG signals. For example, where the extended leads V7, V8, V9, $V_{3R}$, $V_{4R}$, and $V_{5R}$ are calculated from the ECG signals (I, II, V1, V2, V3, V4, V5, and V6) measured by the potential detector of the standard 12-lead electrocardiograph, each extended lead can be expressed by Eq (1-4) below.

$$V_i = \sum_j \alpha_{i,j} V_j \tag{1-4}$$

In the above equation, i indicates a lead number of each extended lead (V7, V8, V9, $V_{3R}$, $V_{4R}$, or $V_{5R}$), and j a lead number of each of the standard 12 leads (I, II, V1, V2, V3, V4, V5, and V6). Furthermore, α stands for transfer coefficients representing the relationship among the leads.

The parameters α in the equation expressed by Eq (1-4) are constants theoretically determined by the torso structure of each individual, but unknowns in Eq (1-4). The parameters α can be determined as a solution of the least-squares computation by actually measuring Leads I, II, V1, V2, V3, V4, V5, and V6 of the standard 12 leads and Leads V7, V8, V9, $V_{3R}$, $V_{4R}$, and $V_{5R}$ of the extended leads in advance and substituting them into Eq (1-5) below.

$$A = (V_j^T V_j)^{-1} V_j^T V_i \quad (1-5)$$

In the above equation, $A = \{\alpha_{i,j}\}$
$V_j = \{V_{s,j}\}$
$V_i = \{V_{i,s}\}$ T represents the transposition of a vector, and s a data sample.

Once the parameters α are determined in this manner, Leads V7, V8, and V9 and Leads $V_{3R}$, $V_{4R}$, $V_{5R}$ of the extended leads can be readily determined immediately from the ECG signals to derive the standard 12-lead ECG, based on Eq (1-4).

Accordingly, the ECG signals of the extended lead ECG except for the standard 12-lead ECG can be easily derived by the arithmetic operation, from the ECG signals of the standard 12-lead ECG measured by the potential detector.

(Configuration of Electrocardiograph with Function for Deriving Extended Lead ECG)

FIG. 1 is a system configuration diagram of an electrocardiograph with an extended lead function for deriving the ECG signals of the extended lead ECG from the ECG signals of the standard 12-lead ECG in the first embodiment. In FIG. 1, specifically, reference numeral 10 denotes a potential detector for detecting the ECG signals of the standard 12-lead ECG. This potential detector 10 functions as a bioamplifier and as an A/D converter for measuring the ECG signals (I, II, V1, V2, V3, V4, V5, and V6) from the electrodes (RA, LA, RL, LL, V1, V2, V3, V4, V5, and V6) mounted on a body surface of a living body for acquisition of the lead waveforms of the standard 12-lead ECG.

Each of the ECG signals (I, II, V1, V2, V3, V4, V5, and V6) of the standard 12 leads detected by the potential detector 10 is stored in an ECG signal memory 12 and fed to a standard 12-lead ECG waveform output device 14. The ECG signals (I, II, V1, V2, V3, V4, V5, and V6) stored in the ECG signal memory 12 are also fed to an extended lead ECG calculator 16. The extended lead ECG calculator 16 performs an arithmetic operation to calculate the ECG signals (V7, V8, and V9) of the extended lead ECG, based on the calculation parameters α set in advance in a memory 15 described later, and outputs them to an extended lead ECG waveform output device 18.

The ECG waveform outputs from the standard 12-lead ECG waveform output device 14 and from the extended lead ECG waveform output device 18 are then fed each to a display monitor 20. Then the display monitor 20 simultaneously displays the standard 12-lead ECG and the extended lead ECG.

The calculation parameters α herein may be values of an average model obtained from the population. Specifically, the ECG signals consisting of the lead potentials (I, II, V1, V2, V3, V4, V5, and V6) of the standard 12 leads and the lead potentials (V7, V8, V9, $V_{3R}$, $V_{4R}$, $V_{5R}$) of the extended leads are collected from the population of patients, healthy individuals, etc. by the potential detector 10, to construct a database in the extended lead ECG calculator 16. Then the extended lead ECG calculator 16 calculates the calculation parameters α of the average model from the data in the database and stores the values α in the memory 15. The calculation parameters α can be calculated based on the aforementioned Eq (1-5).

Figure 2:
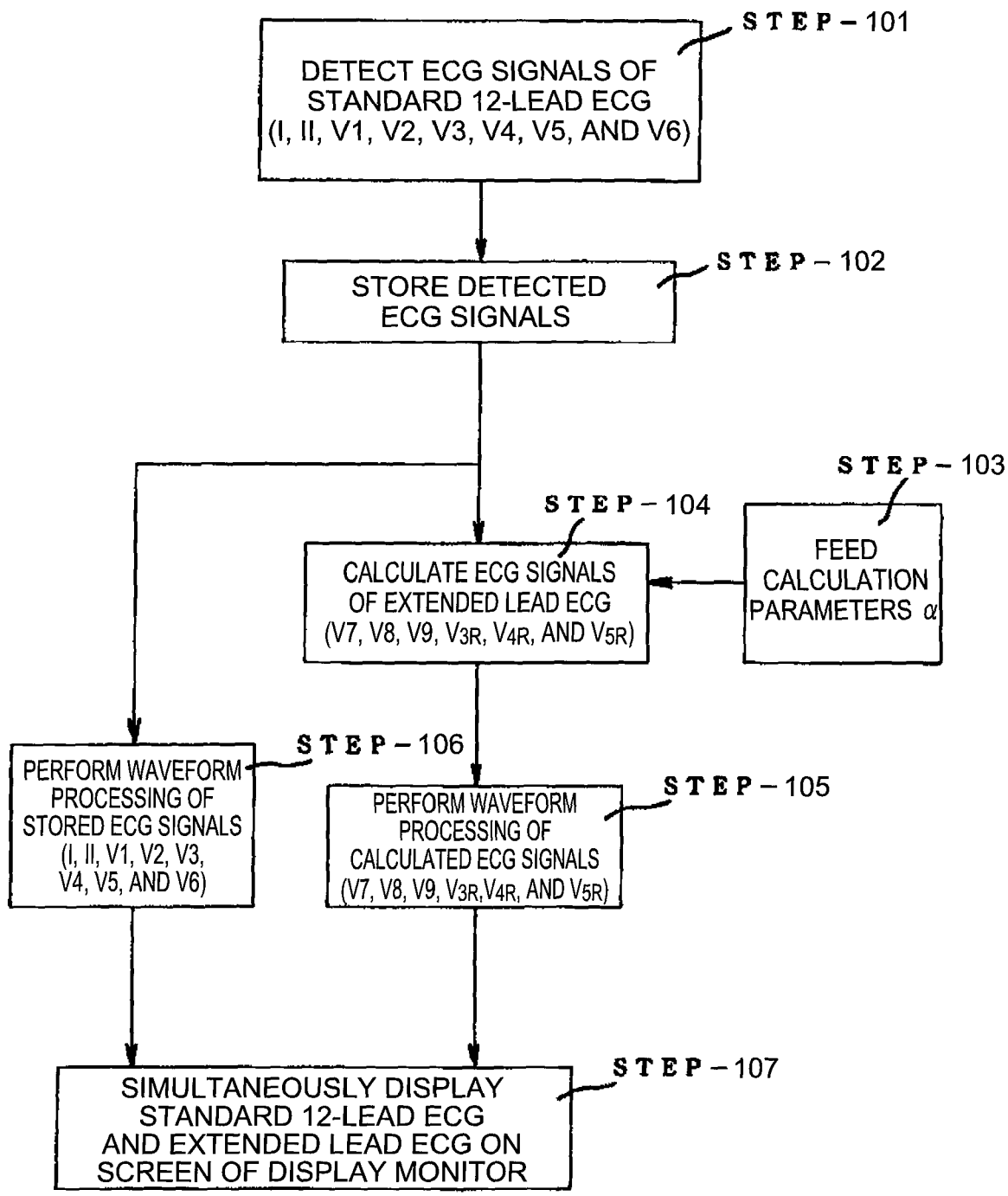
FIG. 2 is a flowchart showing the operation of the electrocardiograph shown in FIG. 1.

The system operation of the electrocardiograph with the extended lead function constructed as described above will be described below with reference to the flowchart shown in FIG. 2.

Specifically, in the electrocardiograph with the extended lead function in the first embodiment, the potential detector 10 first measures the ECG signals (I, II, V1, V2, V3, V4, V5, and V6) of the standard 12-lead ECG of a patient (STEP-101). The ECG signals of the standard 12-lead ECG thus measured are stored into the ECG signal memory 12 (STEP-102). Then the calculation parameters α preliminarily set in the memory 15 are fed to the extended lead ECG calculator 16 (STEP-103). Thereafter, the extended lead ECG calculator 16 performs the arithmetic operation to calculate the ECG signals (V7, V8, V9, $V_{3R}$, $V_{4R}$, and $V_{5R}$) of the extended lead ECG based on the patient's ECG signals stored in the ECG signal memory 12 and the calculation parameters α (STEP-104). This arithmetic operation to calculate the ECG signals (V7, V8, V9, $V_{3R}$, $V_{4R}$, and $V_{5R}$) of the extended lead ECG by the extended lead ECG calculator 16 can be performed according to Eqs (1-6) to (1-11) below, based on the aforementioned Eq (1-4).

Lead V7: $V_7 = \alpha_{7I} V_I + \alpha_{7II} V_{II} + \alpha_{7V1} V_{V1} + \alpha_{7V2} V_{V2} + \ldots + \alpha_{7V6} V_{V6}$ (1-6)

Lead V8: $V_8 = \alpha_{8I} V_I + \alpha_{8II} V_{II} + \alpha_{8V1} V_{V1} + \alpha_{8V2} V_{V2} + \ldots + \alpha_{8V6} V_{V6}$ (1-7)

Lead V9: $V_9 = \alpha_{9I} V_I + \alpha_{9II} V_{II} + \alpha_{9V1} V_{V1} + \alpha_{9V2} V_{V2} + \ldots + \alpha_{9V6} V_{V6}$ (1-8)

Lead $V_{3R}$: $V_{3R} = \alpha_{3RI} V_I + \alpha_{3RII} V_{II} + \alpha_{3RV1} V_{V1} + \alpha_{3RV2} V_{V2} + \ldots + \alpha_{3RV6} V_{V6}$ (1-9)

Lead $V_{4R}$: $V_{4R} = \alpha_{4RI} V_I + \alpha_{4RII} V_{II} + \alpha_{4RV1} V_{V1} + \alpha_{4RV2} V_{V2} + \ldots + \alpha_{4RV6} V_{V6}$ (1-10)

Lead $V_{5R}$: $V_{5R} = \alpha_{5RI} V_I + \alpha_{5RII} V_{II} + \alpha_{5RV1} V_{V1} + \alpha_{5RV2} V_{V2} + \ldots + \alpha_{5RV6} V_{V6}$ (1-11)

The ECG signals (V7, V8, V9, $V_{3R}$, $V_{4R}$, and $V_{5R}$) of the extended lead ECG calculated in this manner are then subjected to waveform processing by the extended lead ECG waveform output device 18 (STEP-105) and the ECG signals (I, II, V1, V2, V3, V4, V5, and V6) of the standard 12-lead ECG stored in the ECG signal memory 12 are subjected to waveform processing by the standard 12-lead ECG waveform output device 14 (STEP-106), and the results are fed each to the display monitor 20. The display monitor 20 simultaneously displays the standard 12-lead ECG and the extended lead ECG thus fed, on a display screen (STEP-107).

Figure 3:
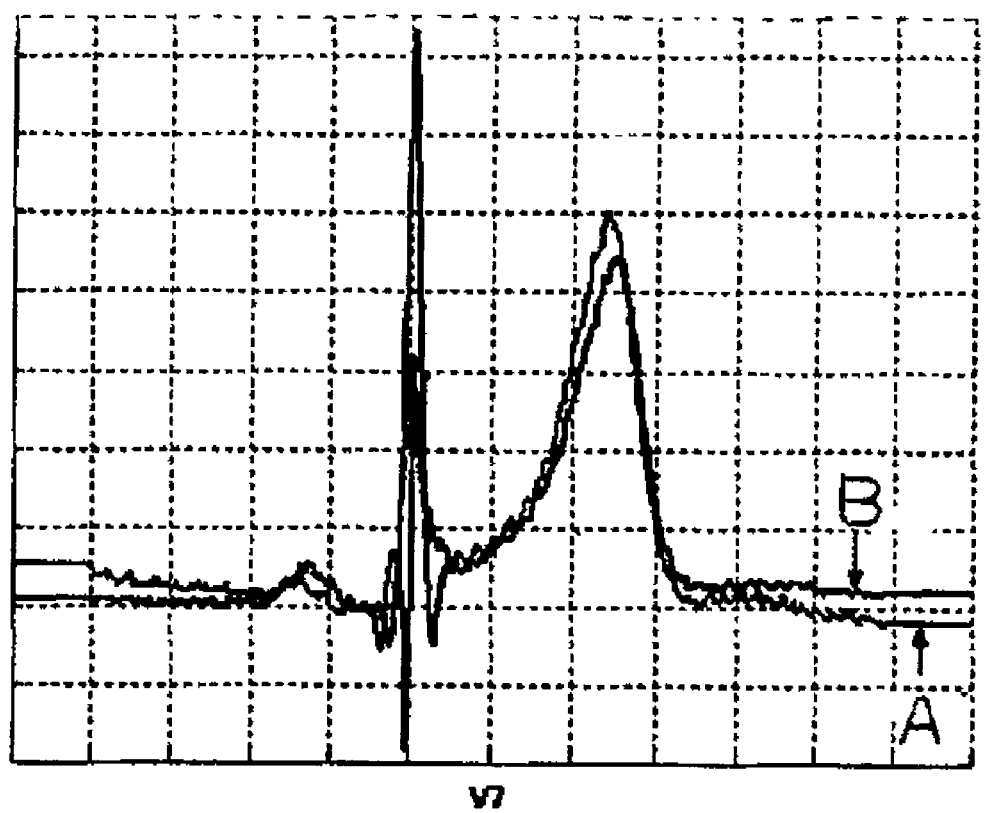
FIG. 3 is a waveform diagram for comparison between an extended lead ECG of Lead V7 derived in the first embodiment and an extended lead ECG based on measured values.
Figure 4:
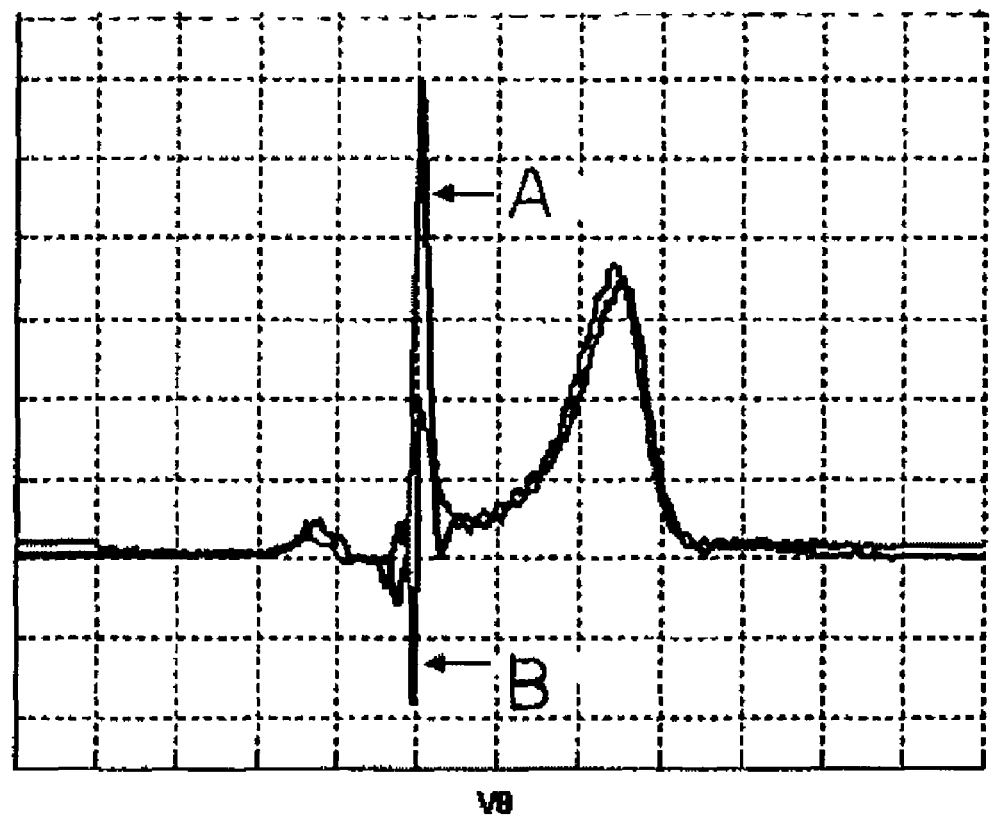
FIG. 4 is a waveform diagram for comparison between an extended lead ECG of Lead V8 derived in the first embodiment and an extended lead ECG based on measured values.
Figure 5:
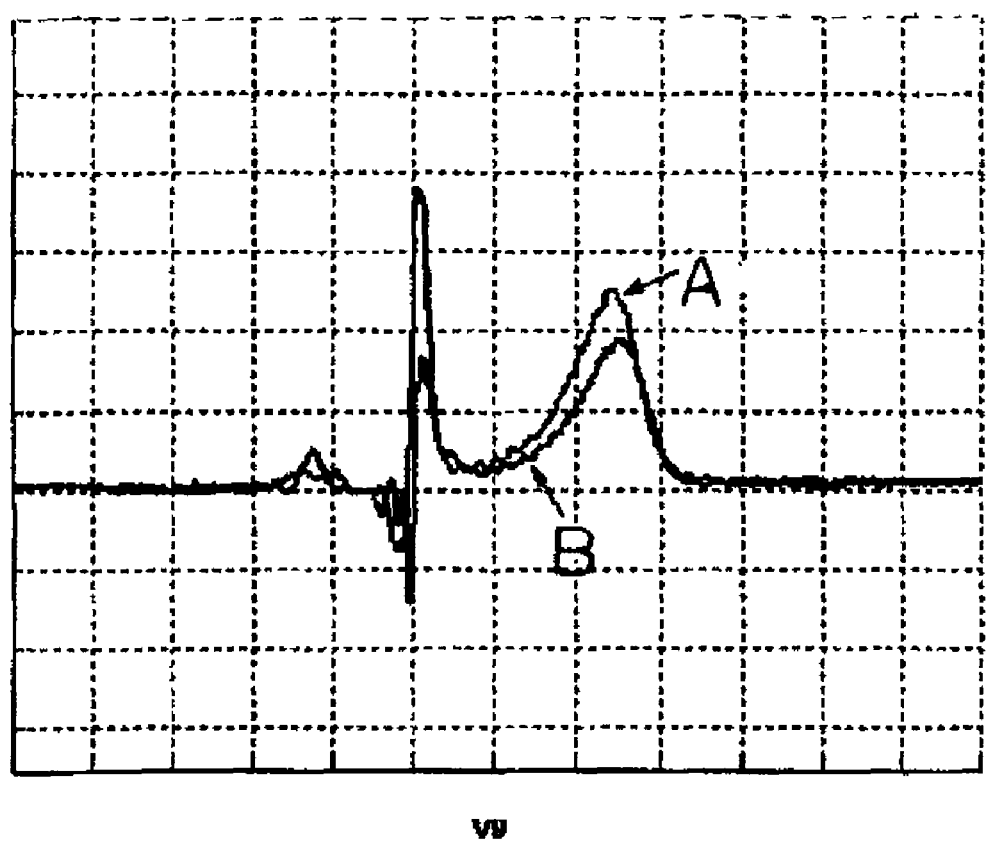
FIG. 5 is a waveform diagram for comparison between an extended lead ECG of Lead V9 derived in the first embodiment and an extended lead ECG based on measured values.

A comparison was made between the extended lead ECG consisting of Leads V7, V8, and V9 calculated from the ECG signals of the standard 12-lead ECG on the basis of the first embodiment and the extended lead ECG based on actually measured values of respective Leads V7, V8, and V9, and the results of the comparison are as illustrated in FIGS. 3 to 5. FIG. 3 shows the ECGs of Lead V7, FIG. 4 the ECGs of Lead V8, and FIG. 5 the ECGs of Lead V9. It is confirmed from each drawing that the ECG (characteristic waveform A) based on the result of the arithmetic operation is close to the ECG (characteristic waveform B) based on the actually measured values, and this assures extremely high precision. Incidentally, fifty four examples of ECGs were recorded for patients, healthy individuals, etc. in clinical practice, and the statistics thereof demonstrated that the correlation coefficients between the waveforms of the ECGs based on the arithmetic operation results and the ECGs based on the actually measured values were approximately 0.83 (83%) on an average and that the tolerance ratio with the difference in potential within 0.1 mV at the center point of the ST segment was approximately 73%. A close correlation with measurements is also shown similarly by the extended lead ECG waveforms as to Leads $V_{3R}$, $V_{4R}$, and $V_{5R}$.

The method and apparatus for deriving the extended lead ECG in the first embodiment, as described above, are able to easily derive through the arithmetic operation, the ECG signals of the extended lead ECG except for the standard 12-lead ECG, from the ECG signals of the standard 12-lead ECG measured by the potential detector. They are useful, particularly, in improvement in the diagnosis precision of the myocardial infarction for the heart muscle at the posterior wall, at the right lateral wall, or at the inferior wall. The deriving method as described above is able to easily expand the functions of the ECG monitors and Holter electrocardiographs and to achieve improvement in the accuracy of diagnoses, for example, not only of the myocardial infarction at the posterior wall, at the right lateral wall, or at the inferior wall, but also of the pulmonary heart, pulmonary embolus, right ventricular infarction, right ventricular hypertrophy, dextrocardia, other right ventricular stress-related diseases, and so on. It is also feasible to produce these electrocardiographs at low cost.

The first embodiment was described above, but it is noted that the derivation of the extended lead ECG in the present invention is not limited to the derivation of the extended lead ECG of Leads V7, V8, and V9 at the electrode locations on the extensions of the chest leads and Leads V3R, V4R, V5R, and V6R at the electrode locations symmetric with the electrode locations of the chest leads. The present invention is also applicable to derivation of other extended lead ECGs. In addition, numerous design changes can be made without departing from the spirit of the invention.

Second Embodiment

The second embodiment will be described below. The second embodiment is different from the first embodiment in that the extended lead ECG (Leads V7, V8, V9, $V_{3R}$, $V_{4R}$, and $V_{5R}$) is derived by use of the lead vectors, instead of the transfer coefficients α.

(Principle of Method of Deriving Extended Lead ECG Using Lead Vectors)

The principle of the method of deriving the extended lead ECG according to the second embodiment is as described below. In the clinical ECG, according to the lead theory, the cardiac source at an arbitrary time can be expressed by a Fixed Single Dipole, as described above, and a potential (V) at an arbitrary lead location can be determined by Eqs (2-1) to (2-3) below.

$$V = L \cdot H \quad (2\text{-}1)$$

$$H = \begin{pmatrix} hx \\ hy \\ hz \end{pmatrix} \quad (2\text{-}2)$$

$$L = \begin{pmatrix} lx \\ ly \\ lz \end{pmatrix} \quad (2\text{-}3)$$

In the above equations, V represents the potential, H the heart vector, and L a lead vector.

When the measured lead potentials of the standard 12-lead ECG are applied to Eq (2-1), Eq (2-4) below results.

$$\begin{pmatrix} L_I^T \\ L_{II}^T \\ L_1^T \\ L_2^T \\ L_3^T \\ L_4^T \\ L_5^T \\ L_6^T \end{pmatrix} \begin{pmatrix} hx \\ hy \\ hz \end{pmatrix} = \begin{pmatrix} V_I \\ V_{II} \\ V_1 \\ V_2 \\ V_3 \\ V_4 \\ V_5 \\ V_6 \end{pmatrix} \quad (2\text{-}4)$$

In the above equation, T represents the transposition of a vector.

Eq (2-4) reduces to general formula L·H=V, and the heart vector H is derived from this Eq (2-4), obtaining Eq (2-5) below.

$$H = (L^T L)^{-1} L^T V \quad (2\text{-}5)$$

Based on Eq (2-5) above, the potentials V of the extended leads can be determined by Eq (2-6) below.

$$\begin{pmatrix} V_7 \\ V_8 \\ V_9 \\ V_{3R} \\ V_{4R} \\ V_{5R} \end{pmatrix} = \begin{pmatrix} L_7^T \\ L_8^T \\ L_9^T \\ L_{3R}^T \\ L_{4R}^T \\ L_{5R}^T \end{pmatrix} \begin{pmatrix} hx \\ hy \\ hz \end{pmatrix} \quad (2\text{-}6)$$

(Configuration of Electrocardiograph with Function for Deriving Extended Lead ECG)

Figure 6:
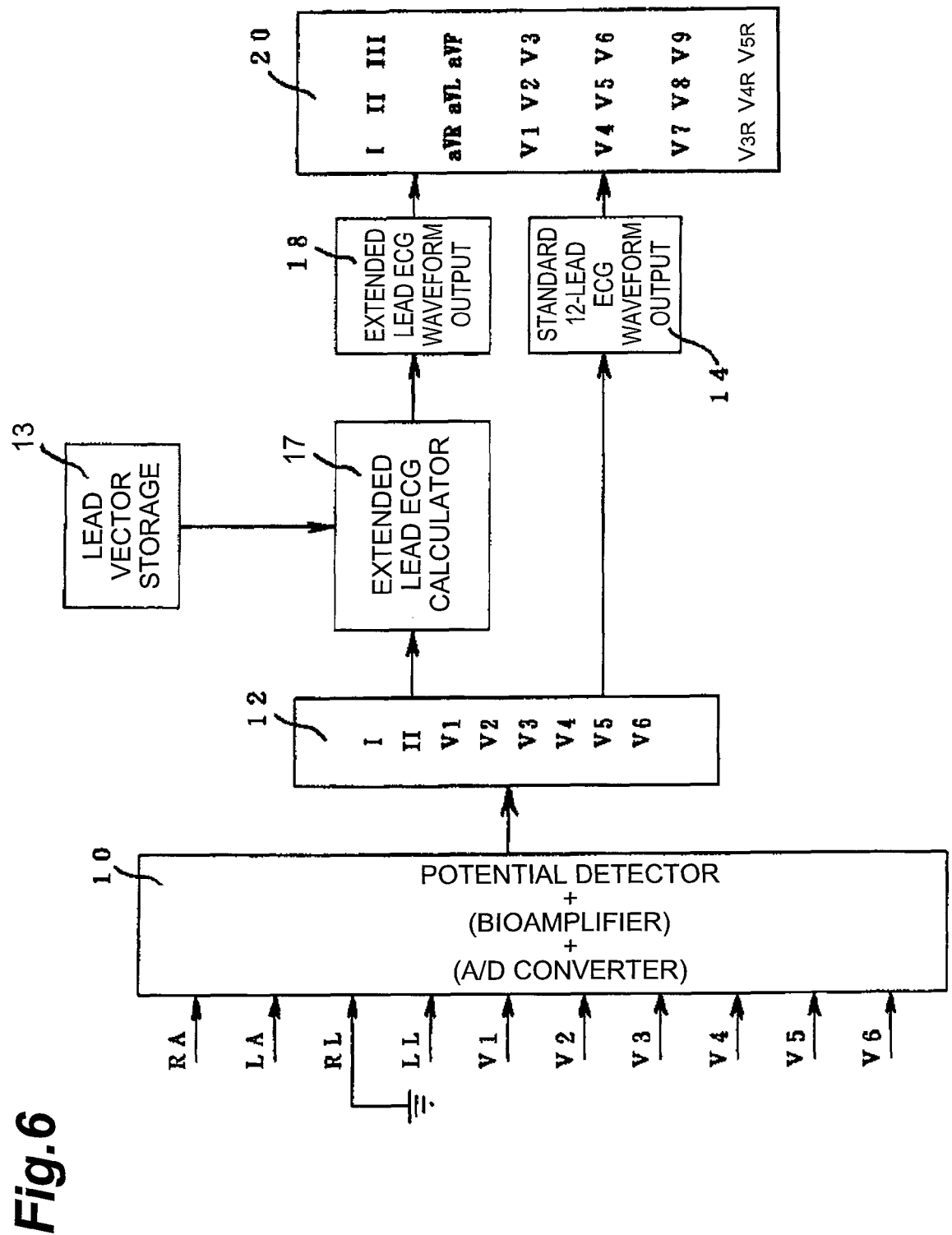
FIG. 6 is a system configuration diagram showing the second embodiment of the electrocardiograph according to the present invention.

FIG. 6 is a system configuration diagram of an electrocardiograph for deriving the ECG signals of the extended lead ECG from the ECG signals of the standard 12-lead ECG in the second embodiment. The electrocardiograph in the second embodiment is different in the arithmetic processing of the extended lead ECG in extended lead ECG calculator 17 from the electrocardiograph in the first embodiment. Specifically, the extended lead ECG calculator 17 receives the ECG signals (I, II, V1, V2, V3, V4, V5, and V6) from the ECG signal memory 12 and then retrieves the lead vectors of I, II, V1, V2, V3, V4, V5, and V6 being the measured leads stored in lead vector storage 13, and determines the heart vector H on the basis of Eq (2-4) and Eq (2-5). Furthermore, the extended lead ECG calculator 17 retrieves the lead vectors L of the extended leads from the lead vector storage 13 and calculates the extended lead ECG (V7, V8, V9, $V_{3R}$, $V_{4R}$, and $V_{5R}$), based on Eq (2-6).

Figure 7:
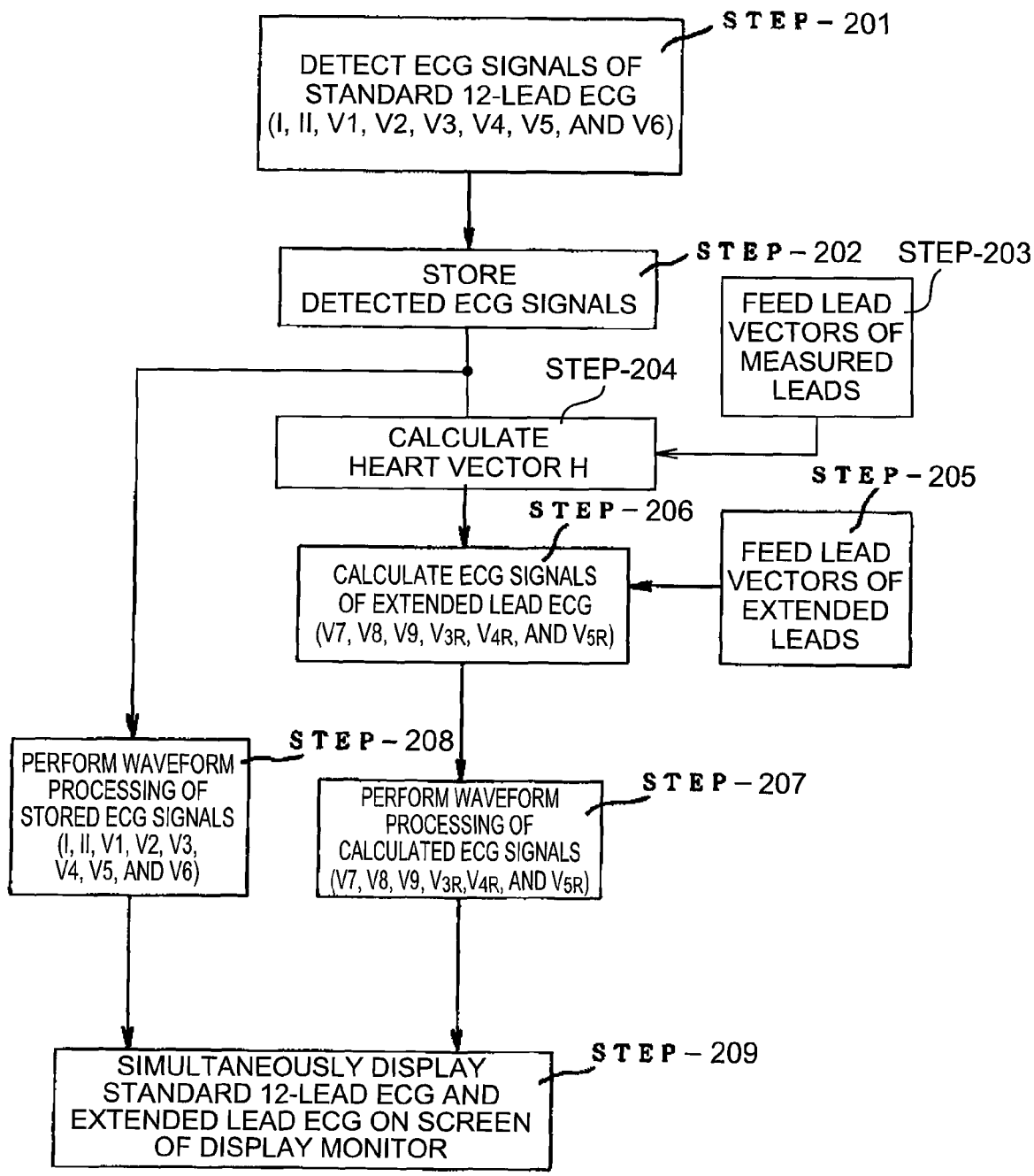
FIG. 7 is a flowchart showing the operation of the electrocardiograph shown in FIG. 6.

The operation of the electrocardiograph shown in FIG. 6 will be described below with reference to the flowchart of the electrocardiograph shown in FIG. 7. First, the potential detector 10 measures the ECG signals (I, II, V1, V2, V3, V4, V5, and V6) of the standard 12-lead ECG of a patient (STEP-201). The ECG signals of the standard 12-lead ECG thus measured are stored into the ECG signal memory 12 (STEP-202). Then the ECG signals (I, II, V1, V2, V3, V4, V5, and V6) stored in the ECG signal memory 12 are fed to the extended lead ECG calculator 17. The extended lead ECG calculator 17 retrieves the lead vectors of I, II, V1, V2, V3, V4, V5, and V6 of the measured leads from the lead vector storage 13 (STEP-203). Then the extended lead ECG calculator 17 determines the heart vector H on the basis of Eq (2-4) and Eq (2-5), using the lead vectors of I, II, V1, V2, V3, V4, V5, and V6 (STEP-204). Furthermore, the lead vectors of the extended leads ($L_7^T$, $L_8^T$, $L_9^T$, $L_{3R}^T$, $L_{4R}^T$, and $L_{5R}^T$) are fed from the lead vector storage 13 into the extended lead ECG calculator 17 (STEP-205). Thereafter, the extended lead ECG calculator 17 calculates the extended lead ECG (V7, V8, V9, $V_{3R}$, $V_{4R}$, and $V_{5R}$) from the heart vector H and the lead vectors of the extended leads, based on Eq (2-6) (STEP-206).

The ECG signals (V7, V8, V9, $V_{3R}$, $V_{4R}$, and $V_{5R}$) of the extended lead ECG calculated in this manner are outputted to the extended lead ECG waveform output device 18 and subjected to waveform processing by the extended lead ECG waveform output device 18, and the result is fed to the display monitor 20 (STEP-207). The ECG signals (I, II, V1, V2, V3, V4, V5, and V6) of the standard 12-lead ECG stored in the ECG signal memory 12 are also outputted to the standard 12-lead ECG waveform output device 14 and subjected to waveform processing by this standard 12-lead ECG waveform output device 14, and the result is fed to the display monitor 20 (STEP-208). The display monitor 20 simultaneously displays on a display screen, the standard 12-lead ECG and the extended lead ECG thus fed (STEP-209).

The method and apparatus for deriving the extended lead ECG in the second embodiment, as described above, are able to easily derive through the arithmetic operation, the ECG signals of the extended lead ECG except for the standard 12-lead ECG, from the ECG signals of the standard 12-lead ECG measured by the potential detector, as in the first embodiment. They are useful, particularly, in improvement in the diagnosis precision of the myocardial infarction for the heart muscle at the posterior wall, at the right lateral wall, or at the inferior wall. The deriving method as described above is able to easily expand the functions of the ECG monitors and Holter electrocardiographs and to achieve improvement in the accuracy of diagnoses, for example, not only of the myocardial infarction at the posterior wall, at the right lateral wall, or at the inferior wall, but also of the pulmonary heart, pulmonary embolus, right ventricular infarction, right ventricular hypertrophy, dextrocardia, other right ventricular stress-related diseases, and so on. It is also feasible to produce these electrocardiographs at low cost.

Third Embodiment

In view of the invention in Patent Document 1 by the Inventor, Leads I and II of the limb leads and the two leads of Leads V2 and V4 of the chest leads in the standard 12-lead ECG are used as the subset of the lead system consisting of the minimum number of channels, for example, with the potential detector consisting of six electrodes to determine (1) Lead III and Leads aV (Lead aVR, Lead aVL, and Lead aVF) by the arithmetic operation based on the characteristic relationship among the leads presented in [Table 1] above. In addition, (2) the rest leads of the chest leads, Leads V1, V3, V5, and V6, are determined by the arithmetic operation based on the relationship among the potentials [V], lead vectors [L], and heart vector [H].

In the third embodiment, therefore, the extended lead potentials (ECG signals of V7, V8, V9 and $V_{3R}$, $V_{4R}$, $V_{5R}$) of the extended lead ECG except for the standard 12-lead ECG are calculated by an arithmetic operation from the standard lead potentials (ECG signals of I, II, V2, and V4) of the standard 12-lead ECG measured by the potential detector consisting of ten or less electrodes.

In this case, in order to detect the ECG signals of Leads I and II among the standard lead potentials of the standard 12-lead ECG, the electrodes are mounted at four locations, the left and right arms (electrodes LA, RA) and the left and right lower limbs (electrodes LL, RL), for the limb leads. In the case of an exercise stress test or the like, the electrodes are mounted at four locations, the distal sites of the left and right clavicles as left and right upper limbs and the left and right sides of the abdomen as left and right lower limbs, to measure the limb leads among the Mason-Likar modified 12 leads as a modification of the standard 12 leads. The electrode RL serves as a ground electrode. Furthermore, in order to measure the ECG signals of two leads (V2, V4) of the chest leads among the standard lead potentials, the electrodes are mounted at two locations: e.g., the fourth rib intercostal space at the left margin of sternum (to obtain the ECG signal of V2) and an intersection between the midline of the left clavicle and a horizontal line traversing the fifth intercostal space (to obtain the ECG signal of V4). In this manner, using the subset (part) of the lead system of the standard 12-lead ECG, the other lead potentials (ECG signals) of the standard 12-lead ECG can be determined based on the characteristic relationship among the leads presented in [Table 1] above or based on the relationship among the potential vector, the lead vector, and the heart vector. The measurement with the subset of modified 12 leads also allows us to obtain the modified 12-lead ECG and extended lead ECG thereof in the same manner. An embodiment of the deriving method of the extended lead ECG and the electrocardiograph with the extended lead function will be specifically described below.

(Principle of Method of Deriving Extended Lead ECG from Lead Vectors)

The principle of the deriving method of the extended lead ECG according to the third embodiment is as described below. In the clinical ECG, as described previously, the cardiac source at an arbitrary time can be expressed by a Fixed Single Dipole according to the lead theory and a potential (V) at an arbitrary lead location can be determined by Eqs (3-1) to (3-3) below.

$$V = L \cdot H \quad (3\text{-}1)$$

$$H = \begin{pmatrix} hx \\ hy \\ hz \end{pmatrix} \quad (3\text{-}2)$$

$$L = \begin{pmatrix} lx \\ ly \\ lz \end{pmatrix} \quad (3\text{-}3)$$

In the above equations, V represents a potential, H the heart vector, and L a lead vector.

Since the heart vector H is a spatial vector fixed in position, it has only three independent parameters. Therefore, the parameters of the heart vector H can be determined from three leads having spatial information. It follows that once the heart vector H is determined, the potentials of the remaining leads of the 12 leads can also be determined by calculation.

For example, the lead potentials of the extended leads (V7, V8, V9, $V_{3R}$, $V_{4R}$, and $V_{5R}$) can be derived by an arithmetic operation as expressed by Eq (3-4) below, based on the measurement of ECG signals of the lead locations (I, II, V2, and V4) as standard lead potentials of the standard 12-lead ECG.

$$\begin{pmatrix} L_I^T \\ L_{II}^T \\ L_2^T \\ L_4^T \end{pmatrix} \begin{pmatrix} hx \\ hy \\ hz \end{pmatrix} = \begin{pmatrix} V_I \\ V_{II} \\ V_2 \\ V_4 \end{pmatrix} \quad (3\text{-}4)$$

In this equation, T represents the transposition of a vector.

Eq (3-4) reduces to the general formula L·H=V. Therefore, the heart vector H is determined from this Eq (3-4) to obtain Eq (3-5) below.

$$H = (L^T L)^{-1} L^T V \quad (3\text{-}5)$$

The potentials V of the extended leads can be determined by Eq (3-6) below, based on above Eq (3-5).

$$\begin{pmatrix} V_7 \\ V_8 \\ V_9 \\ V_{3R} \\ V_{4R} \\ V_{5R} \end{pmatrix} = \begin{pmatrix} L_7^T \\ L_8^T \\ L_9^T \\ L_{3R}^T \\ L_{4R}^T \\ L_{5R}^T \end{pmatrix} \begin{pmatrix} hx \\ hy \\ hz \end{pmatrix} \quad (3\text{-}6)$$

[Configuration of Electrocardiograph with Function for Deriving Extended Lead ECG]

Figure 8:
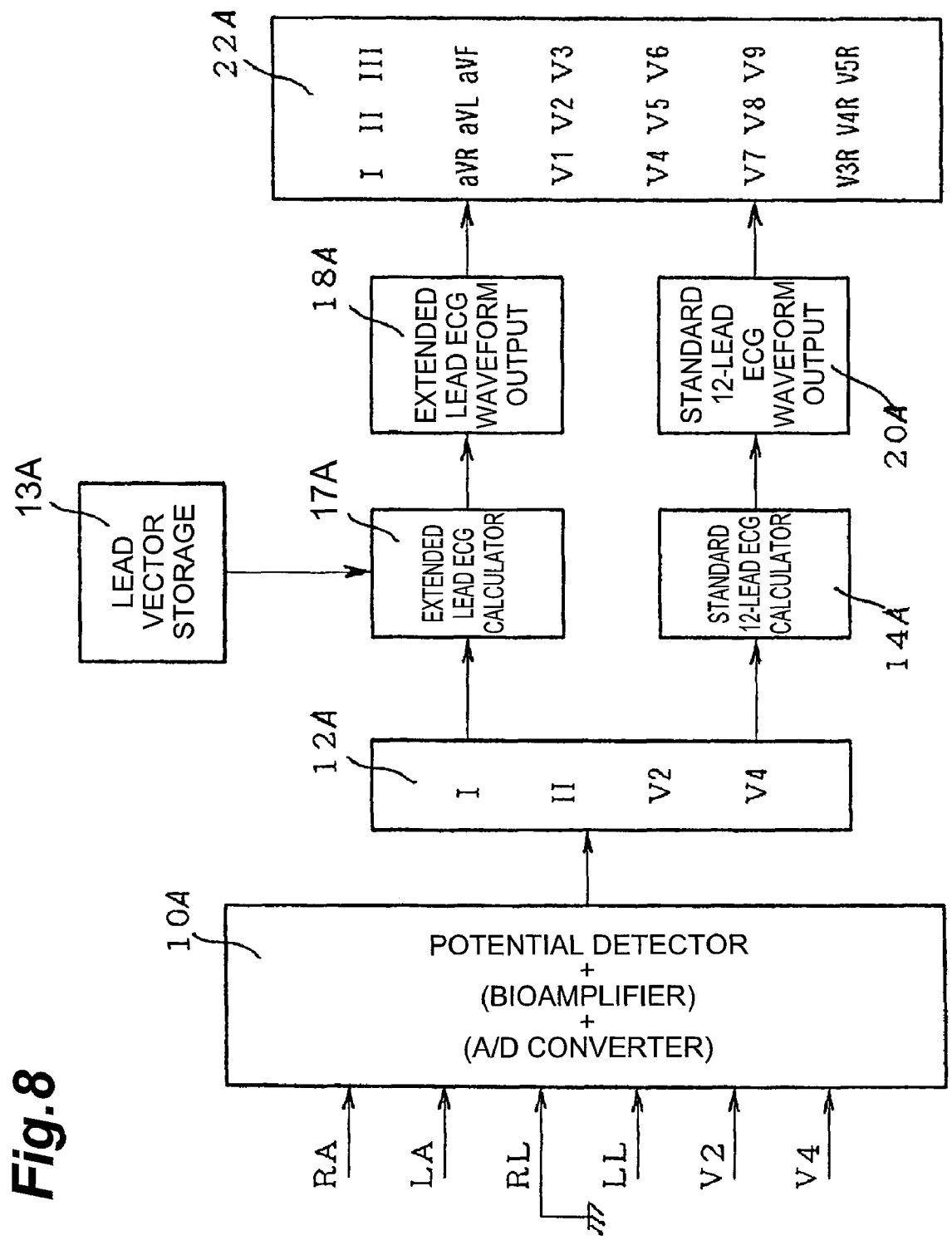
FIG. 8 is a system configuration diagram showing the third embodiment of the electrocardiograph according to the present invention.

FIG. 8 is a system configuration diagram of an electrocardiograph with a function of deriving an extended lead ECG in the third embodiment. In FIG. 8, specifically, reference symbol 10A denotes a potential detector for measuring the ECG signals as standard lead potentials of the standard 12-lead ECG. This potential detector 10A functions as a bioamplifier and as an A/D converter for measuring the ECG signals (I, II, V2, and V4) from ten or less electrodes mounted on a body surface of a living body for obtaining the standard lead potentials of the standard 12-lead ECG, i.e., the subset of the potential detector for the standard 12-lead ECG (e.g., the six electrodes of RA, LA, RL, LL, V2, and V4).

The ECG signals (I, II, V2, and V4) of the standard 12-lead potentials detected by this potential detector 10A are stored each into the ECG signal memory 12A and fed to a standard 12-lead ECG calculator 14A. The ECG signals (I, II, V2, and V4) stored in this ECG signal memory 12A are also fed to an extended lead ECG calculator 17A. Then the extended lead ECG calculator 17A retrieves the lead vectors of I, II, V2, and V4 being the measured leads stored in a lead vector storage 13A, and determines the heart vector [H] on the basis of Eq (3-4) and Eq (3-5). Furthermore, the extended lead ECG calculator 17A retrieves the extended lead vectors [L] ($L_7^T$, $L_8^T$, $L_9^T$, $L_{3R}^T$, $L_{4R}^T$, and $L_{5R}^T$) from the lead vector storage 13A and performs an arithmetic operation to calculate the ECG signals (V7, V8, V9, $V_{3R}$, $V_{4R}$, and $V_{5R}$) as extended lead potentials of the extended lead ECG on the basis of Eq (3-6).

The ECG signals as extended lead potentials calculated in this manner by the extended lead ECG calculator 17A are fed to an extended lead ECG waveform output device 18A. The standard 12-lead potentials calculated by the standard 12-lead ECG calculator 14A are fed to a standard 12-lead ECG waveform output device 20A.

Then the ECG waveform outputs from the standard 12-lead ECG waveform output device 20A and from the extended lead ECG waveform output device 18A are fed each to a display monitor 22A and are arranged to simultaneously display images of the standard 12-lead ECG and the extended lead ECG.

Figure 9:
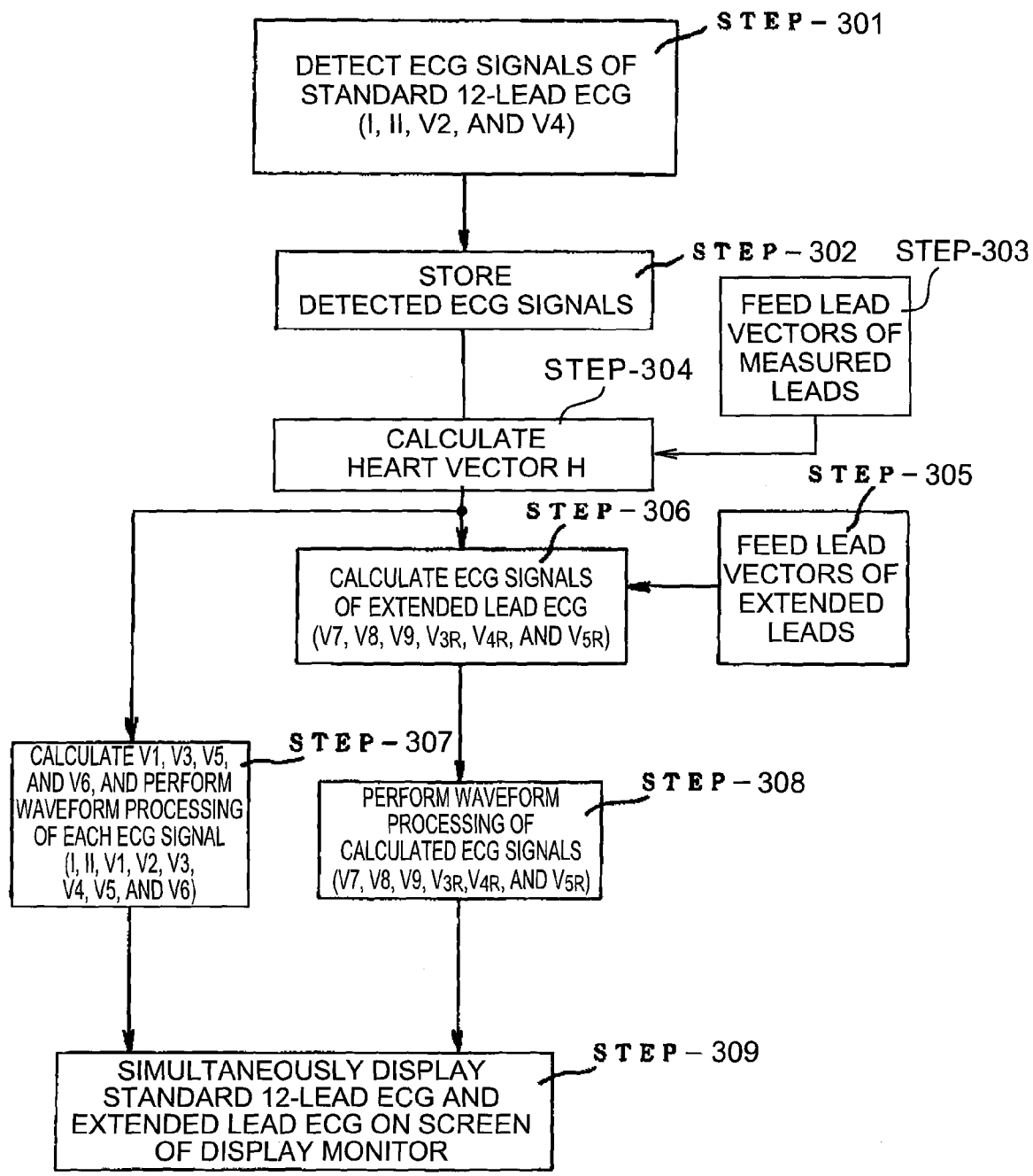
FIG. 9 is a flowchart showing the operation of the electrocardiograph shown in FIG. 8.

The system operation of the electrocardiograph with the extended lead function constructed as described above will be described below with reference to the flowchart shown in FIG. 9.

First, in the electrocardiograph with the extended lead function, the potential detector 10A measures the ECG signals (I, II, V2, and V4) as standard lead potentials of the standard 12-lead ECG of a patient (STEP-301). The ECG signals (I, II, V2, and V4) of the standard lead potentials thus measured are stored into the ECG signal memory 12A (STEP-302).

The extended lead ECG calculator 17A retrieves the lead vectors of I, II, V2, and V4 as the measured leads from the lead vector storage 13A (STEP-303). Furthermore, the extended lead ECG calculator 17A uses these lead vectors of I, II, V2, and V4 to perform an arithmetic operation to calculate the heart vector [H] from Eq (3-4) and Eq (3-5) representing the relationships among the potentials [V], lead vectors [L], and heart vector [H] concerning the leads, based on the ECG signals (I, II, V2, and V4) of the patient stored in the ECG signal memory 12A (STEP-304). The lead vectors ($L_7^T$, $L_8^T$, $L_9^T$, $L_{3R}^T$, $L_{4R}^T$, and $L_{5R}^T$) of the extended leads are fed from the lead vector storage 13A to the extended lead ECG calculator 17A (STEP-305). Thereafter, the extended lead ECG calculator 17A performs an arithmetic operation to calculate the ECG signals (V7, V8, V9, $V_{3R}$, $V_{4R}$, and $V_{5R}$) of the extended lead ECG from the heart vector [H] and the lead vectors of the extended leads, based on Eq (3-6) (STEP-306).

On the other hand, the ECG signals (I, II, V2, and V4) stored in the ECG signal memory 12A are fed to the standard 12-lead ECG calculator 14A, which performs the arithmetic operation to calculate the lead potentials (I, II, III, V1, V2, V3, V4, V5, V6, aVR, aVL, aVF) of the standard 12-lead ECG. Here Leads V1, V3, V5, and V6 are calculated based on the relationship among the potential vector, lead vectors, and heart vector, using the heart vector [H] determined at STEP-304, and the lead vectors ($L_1^T$, $L_3^T$, $L_5^T$, $L_6^T$). The lead potentials of the standard 12-lead ECG calculated by the standard 12-lead ECG calculator 14A are subjected to waveform processing by the standard 12-lead ECG waveform output device 20A and the result is fed to the display monitor 22A (STEP-307).

Then the ECG signals (V7, V8, V9, $V_{3R}$, $V_{4R}$, and $V_{5R}$) as extended lead potentials of the extended lead ECG calculated by the extended lead ECG calculator 17A are subjected to waveform processing by the extended lead ECG waveform output device 18A and the result is fed to the display monitor 22A (STEP-308). Furthermore, the extended lead ECG waveform output and the standard 12-lead ECG waveform output resulting from the waveform processing are simultaneously displayed on a display screen of the display monitor 22A (STEP-309).

Fourth Embodiment

Method of Deriving Extended Lead ECG Making Use of Relationship Among Leads (Transfer Coefficients α)

The lead theory based on the dipole model of the heart is a theory most used in clinical application nowadays. A potential (V) at an arbitrary lead location can be determined by Eqs (4-1) to (4-3) below.

$$V = L \cdot H \quad (4\text{-}1)$$

$$H = \begin{pmatrix} hx \\ hy \\ hz \end{pmatrix} \quad (4\text{-}2)$$

$$L = \begin{pmatrix} lx \\ ly \\ lz \end{pmatrix} \quad (4\text{-}3)$$

In the above equations, V represents a potential matrix, H the heart vector, and L a lead vector.

According to this lead theory, as described above, a heart potential at an arbitrary lead location is determined by three parameters. Therefore, ECG potentials at three or more arbitrary locations on a body surface have a correlation to each other. Specifically, some lead potentials can be expressed by linear combination of the other lead potentials. For example, there is the relationship represented by Eq (4-4) below.

$$V_i = \sum_j \alpha_{i,j} V_j \quad (4\text{-}4)$$

[In the above relationship, i represents a lead number of each extended lead location (V7, V8, V9, $V_{3R}$, $V_{4R}$, or $V_{5R}$), and j a lead number of each standard lead potential of the standard 12 leads (I, II, V2, and V4). α stands for transfer coefficients representing the relationship among the leads.] Theoretically, the transfer coefficients α are constants determined by the torso structure of each individual and are unknowns in above Eq (4-4). On the contrary, however, it is also possible to actually measure the lead potentials at the respective lead locations (V7, V8, V9, $V_{3R}$, $V_{4R}$, $V_{5R}$ and I, II, V2, V4) in advance and to determine the transfer coefficients α, as in Eq (4-5) below, from the above Eq (4-4).

$$A = (V_j^T V_j)^{-1} V_j^T V_i \quad (4\text{-}5)$$

In the above equation, $A = \{\alpha_{i,j}\}$
$V_j = \{V_{s,j}\}$
$V_i = \{V_{i,s}\}$ i represents a lead number of each extended lead location (V7, V8, V9, $V_{3R}$, $V_{4R}$, or $V_{5R}$), j a lead number of each standard lead potential of the standard 12 leads (I, II, V2, and V4), and s a data sample.

Once the transfer coefficients α are determined in this manner, the extended lead potentials (V7, V8, V9, $V_{3R}$, $V_{4R}$, and $V_{5R}$) of the extended lead ECG can be instantly determined from the ECG signals (I, II, V2, and V4) as standard lead potentials of the standard 12-lead ECG, according to Eq (4-5) above.

In the present embodiment, an ideal way for calculation of the extended leads of a specific person is to determine the transfer coefficients α of the specific individual in advance, store them as data, and use them for the arithmetic operation, which can yield the arithmetic operation result with high accuracy. It is, however, not practical in some cases to first determine the transfer coefficients α of the individual, store them as data, and keep them available for the arithmetic operation as needed. In such cases, therefore, the transfer coefficients α of an average human model are determined and are stored as data to be ready for use in the arithmetic operation as needed. For this purpose, for example, ECGs are measured from many people, for example, on the occasion of group medical examination, to collect the ECG signals consisting of the two leads I and II of the limb leads and the two leads V2 and V4 of the chest leads out of the standard 12 leads and the extended lead potentials V7, V8, V9, $V_{3R}$, $V_{4R}$, and $V_{5R}$, and thereby construct a database for calculation of the transfer coefficients α for the arithmetic operation. Then the entire data of the group stored in this database is applied to aforementioned Eq (4-5) to determine average α values and the α values thus obtained are stored into a predetermined memory for feeding them to a calculator for calculating the extended lead potentials.

In the embodiments described above, the derivation of the extended lead ECG was described using Leads V7, V8, V9 at the electrode locations on extensions of the chest leads and Leads V3R, V4R, and V5R at the electrode potentials symmetric with the electrode locations of the chest leads, but, without having to be limited to these, the present invention can also be applied to derivation of other extended lead ECGs. In the embodiments described above, the extended lead ECG was calculated from Leads I, II, V2, and V4 being the standard lead potentials, but, without having to be limited to this, the extended lead ECG can also be calculated by using various combinations of other two limb leads and two chest leads of the standard 12 leads. Particularly, combinations of practical use include a combination of Leads I, II, V2, and V5, a combination of Leads I, II, V2, and V6, a combination of Leads I, II, V1, and V4, a combination of Leads I, II, V1, and V5, and a combination of Leads I, II, V1, and V6.

Described below is an electrocardiograph with the extended lead function arranged to be able to simultaneously display the extended lead ECG and the standard 12-lead ECG on a screen of a display monitor, based on the derivation method of the extended lead ECG described in the fourth embodiment.

[Configuration of Electrocardiograph with Function for Derivation of Extended Lead ECG]

Figure 10:
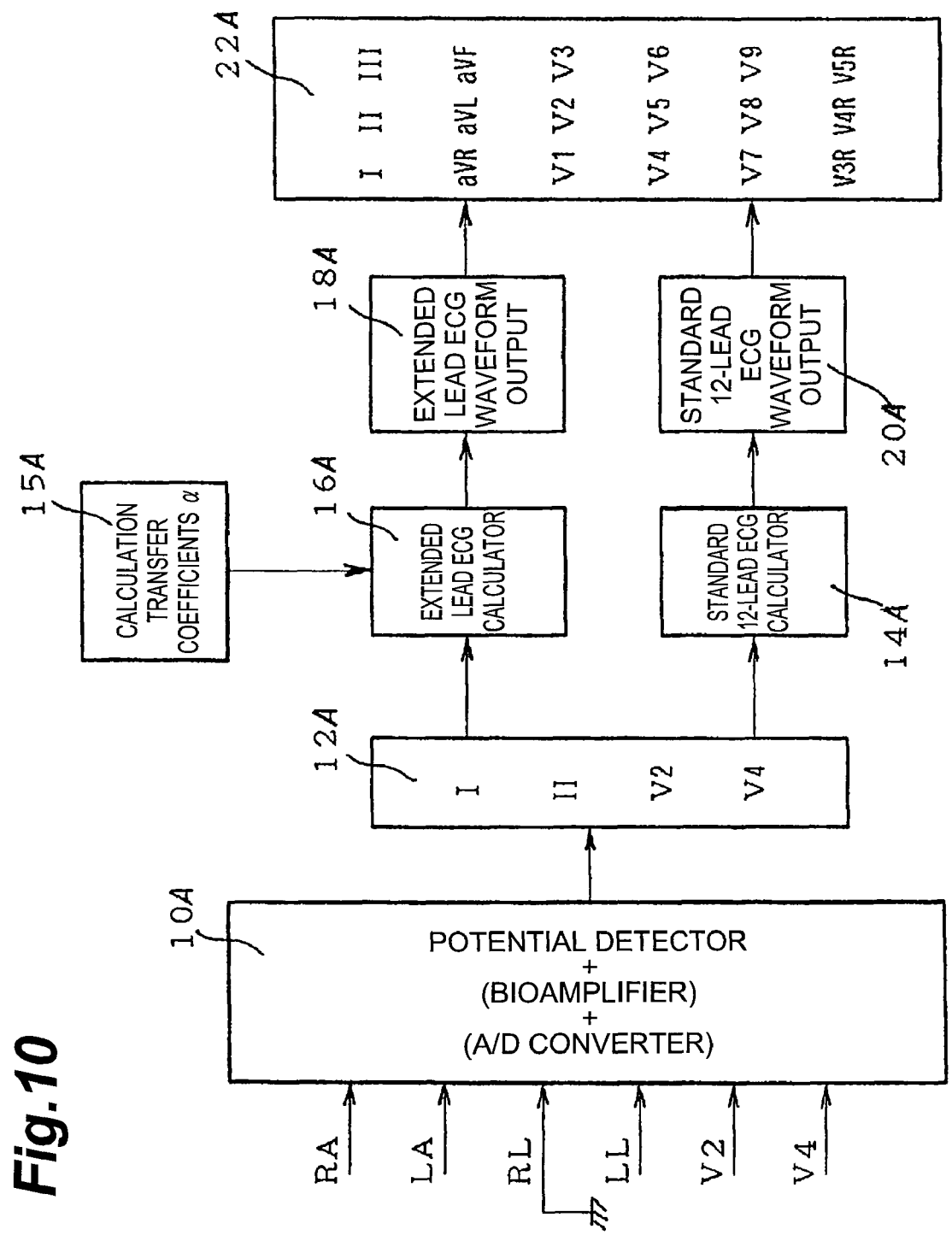
FIG. 10 is a system configuration diagram showing the fourth embodiment of the electrocardiograph according to the present invention.

FIG. 10 is a system configuration diagram of an electrocardiograph with a function of deriving the extended lead ECG in the fourth embodiment. In FIG. 10, specifically, reference symbol 10A denotes a potential detector for measuring the ECG signals as standard lead potentials of the standard 12-lead ECG. This potential detector 10A functions as a bioamplifier and as an A/D converter for measuring the ECG signals (I, II, V2, and V4) from ten or less electrodes mounted on a body surface of a living body for acquisition of the standard lead potentials of the standard 12-lead ECG, i.e., a subset (e.g., the six electrodes of RA, LA, RL, LL, V2, and V4) of the potential detector for the standard 12-lead ECG.

The ECG signals (I, II, V2, and V4) of the standard 12-lead potentials detected by this potential detector 10A are stored each into the ECG signal memory 12A and fed to the standard 12-lead ECG calculator 14A. The ECG signals (I, II, V2, and V4) stored in this ECG signal memory 12A are fed to the extended lead ECG calculator 16A, which performs the arithmetic operation to calculate the ECG signals (V7, V8, V9, $V_{3R}$, $V_{4R}$, and $V_{5R}$) as extended lead potentials of the extended lead ECG.

As described later in detail, the ECG signals (V7, V8, V9, $V_{3R}$, $V_{4R}$, and $V_{5R}$) are calculated according to above Eq (4-1), based on the ECG signals (I, II, V2, and V4) as the standard lead potentials of the standard 12-lead ECG measured, using the transfer coefficients α for the arithmetic operation set in advance in the memory 15A.

The ECG signals as the extended lead potentials calculated in this manner by the extended lead ECG calculator 16A are fed to the extended lead ECG waveform output device 18A. Furthermore, the ECG signals as the standard 12-lead potentials calculated by the standard 12-lead ECG calculator 14A are fed to the standard 12-lead ECG waveform output device 20A.

Then the ECG waveform outputs from the standard 12-lead ECG waveform output device 20A and from the extended lead ECG waveform output device 18A are fed each to the display monitor 22A to display images of the standard 12-lead ECG and the extended lead ECG simultaneously.

For that, the extended lead ECG calculator 16A collects the ECG signals consisting of two Leads I, II of the limb leads and two Leads V2, V4 of the chest leads out of the standard 12 leads, and the extended lead potentials V7, V8, V9, $V_{3R}$, $V_{4R}$, and $V_{5R}$ recorded from a number of patients, healthy individuals, etc. by the potential detector 10A, constructs a database for calculation of the calculation transfer coefficients α of an average model, and stores the calculation transfer coefficients α calculated using the database, into the memory 15A. In this case, the calculation transfer coefficients α can be calculated according to Eq (4-5).

Figure 11:
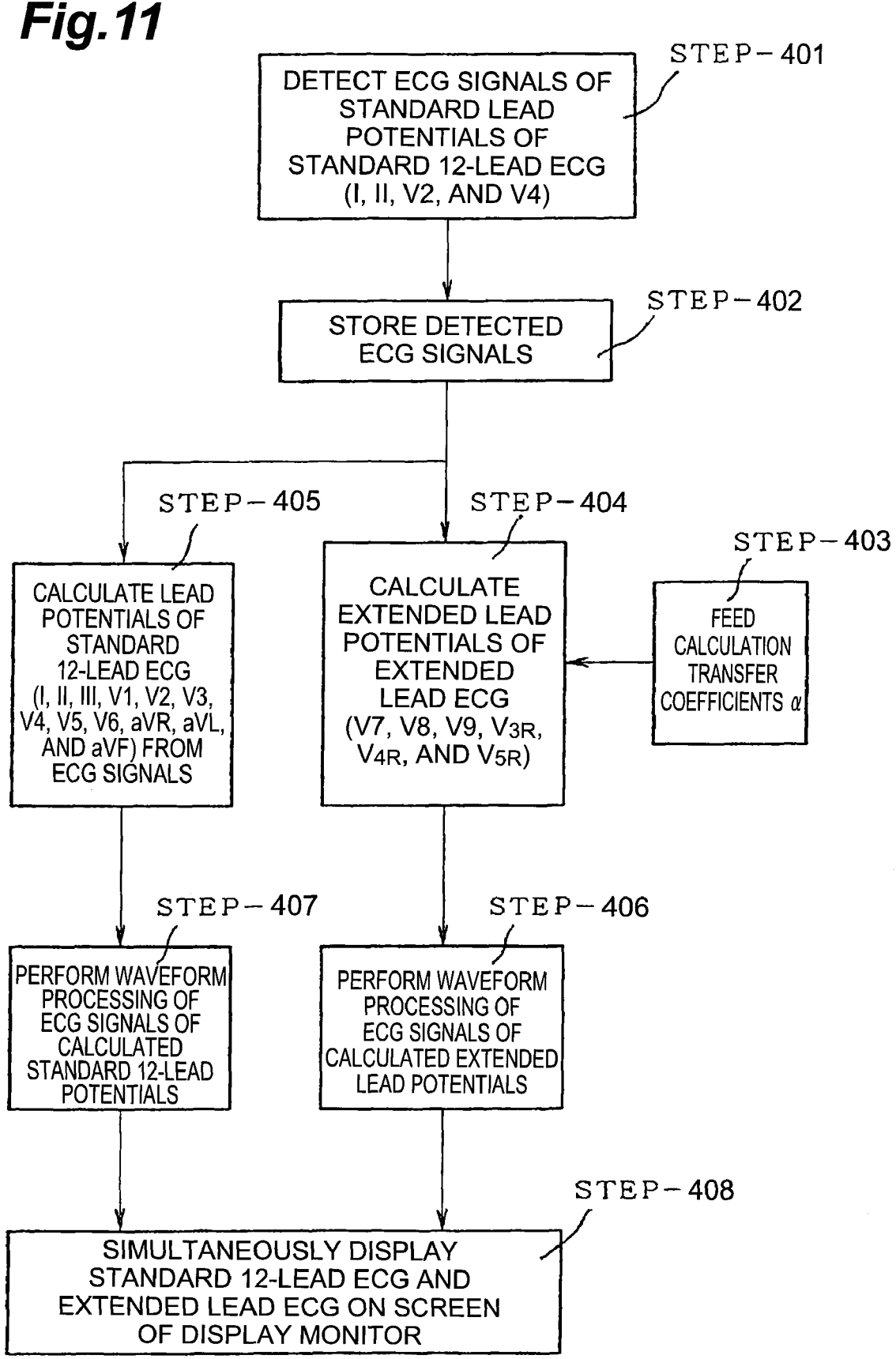
FIG. 11 is a flowchart showing the operation of the electrocardiograph shown in FIG. 9.
Figure 12:
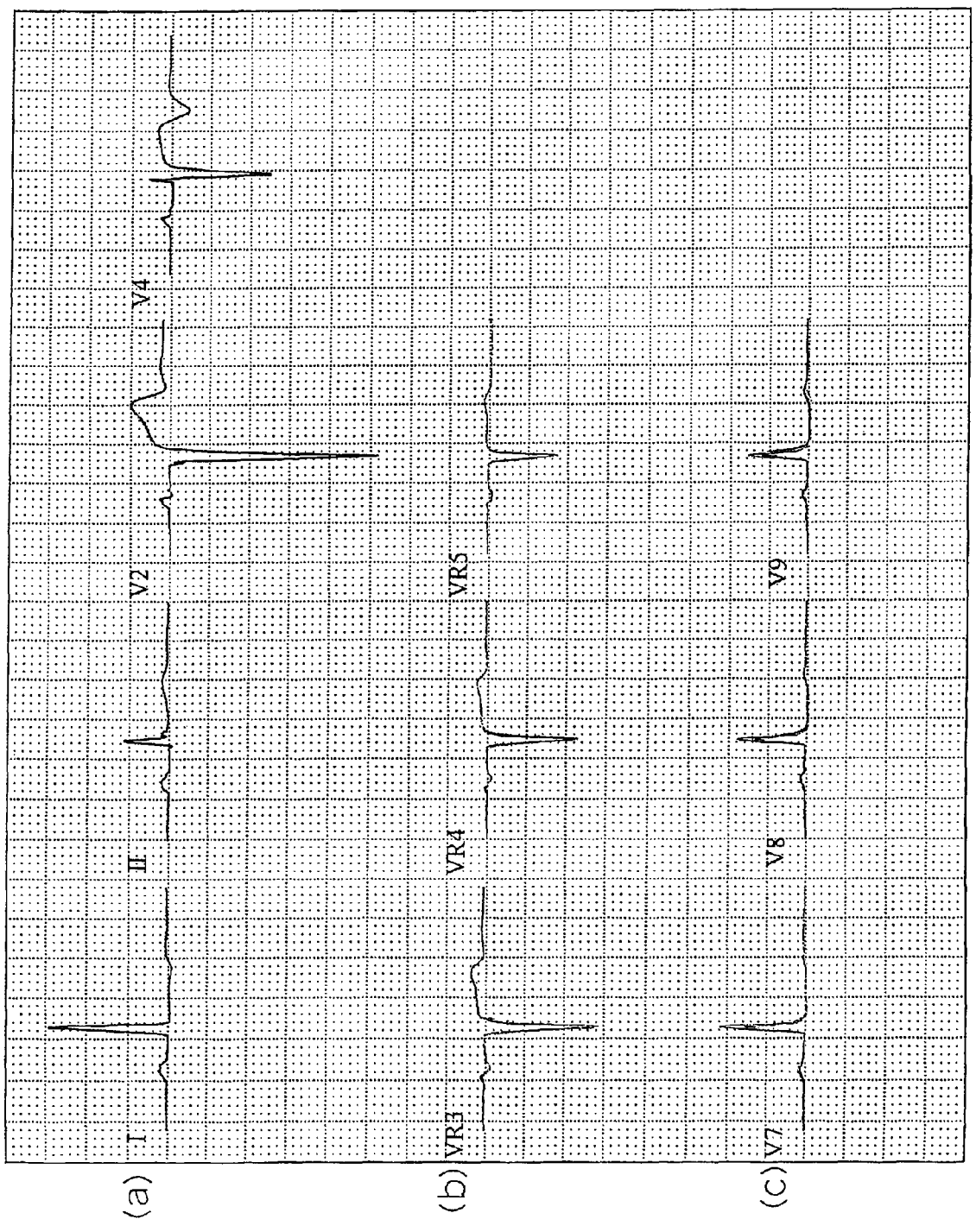
In FIG. 12, (a) shows measured waveforms of ECG signals (I, II, V2, and V4) of the standard 12-lead ECG, (b) calculated waveforms and measured waveforms of Leads V3R, V4R, and V5R of the extended lead ECG, and (c) calculated waveforms and measured waveforms of Leads V7, V8, and V9 of the extended lead ECG.
Figure 13:
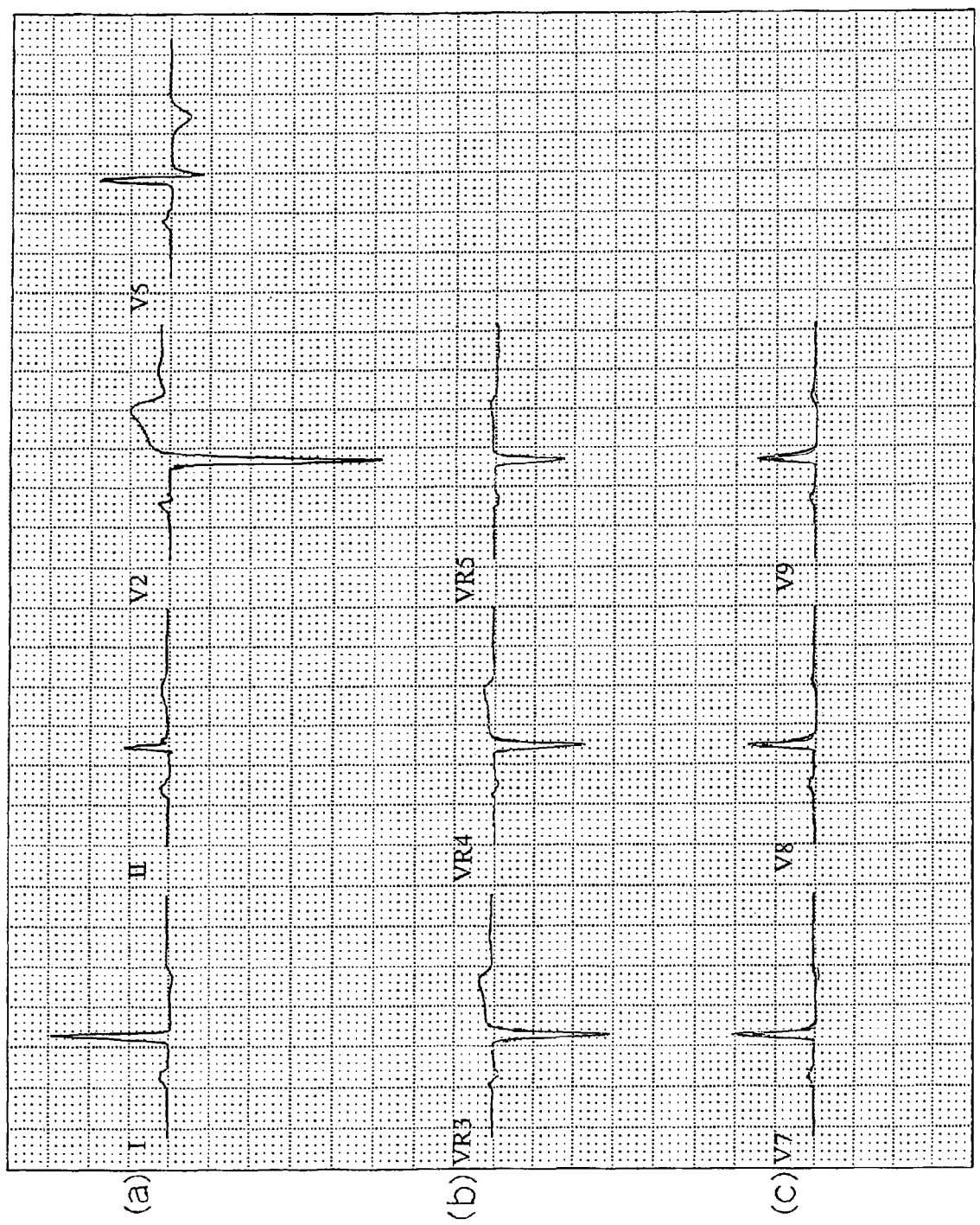
In FIG. 13, (a) shows measured waveforms of ECG signals (I, II, V2, and V5) of the standard 12-lead ECG, (b) calculated waveforms and measured waveforms of Leads V3R, V4R, and V5R of the extended lead ECG, and (c) calculated waveforms and measured waveforms of Leads V7, V8, and V9 of the extended lead ECG.
Figure 14:
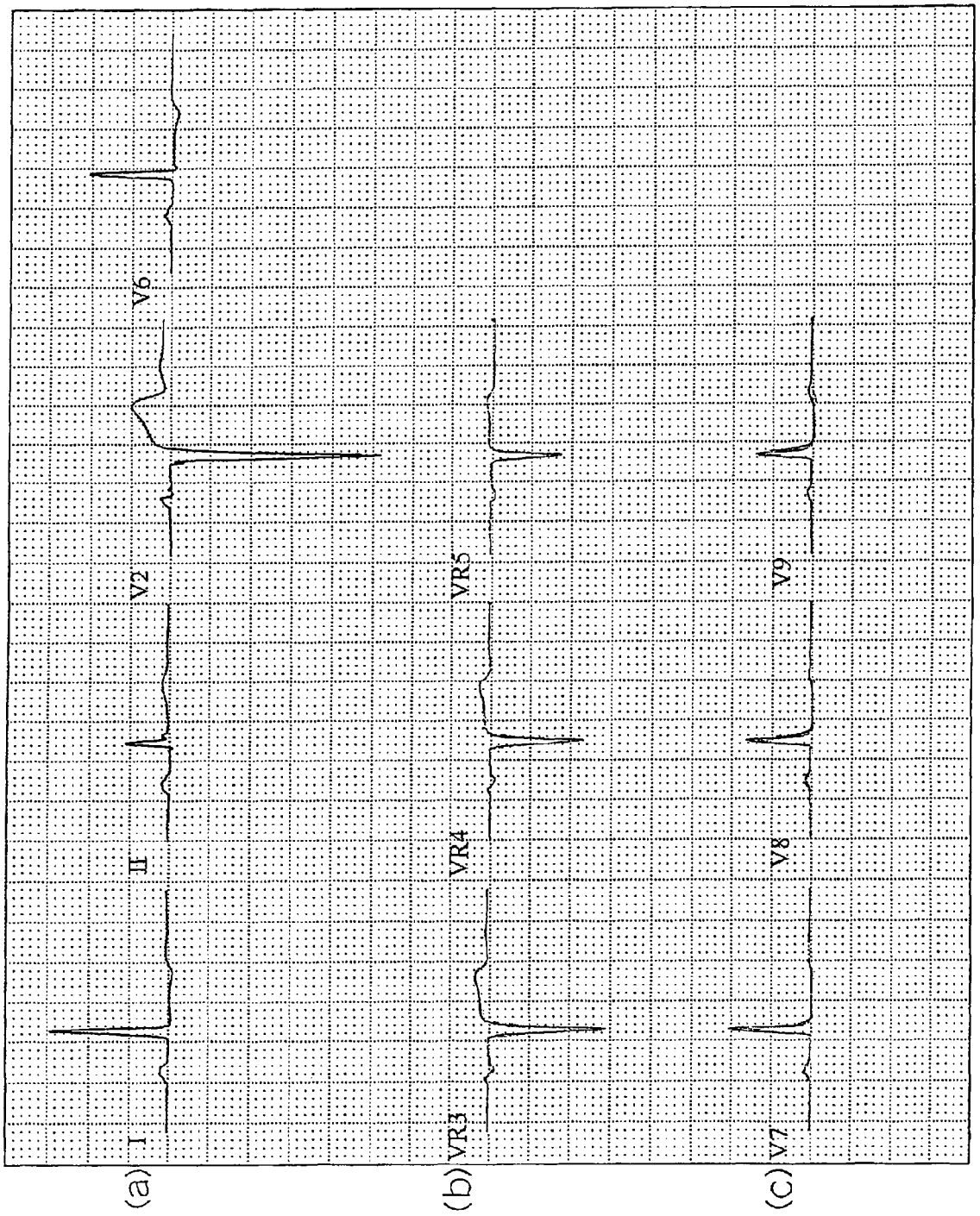
In FIG. 14, (a) shows measured waveforms of ECG signals (I, II, V2, and V6) of the standard 12-lead ECG, (b) calculated waveforms and measured waveforms of Leads V3R, V4R, and V5R of the extended lead ECG, and (c) calculated waveforms and measured waveforms of Leads V7, V8, and V9 of the extended lead ECG.
Figure 15:
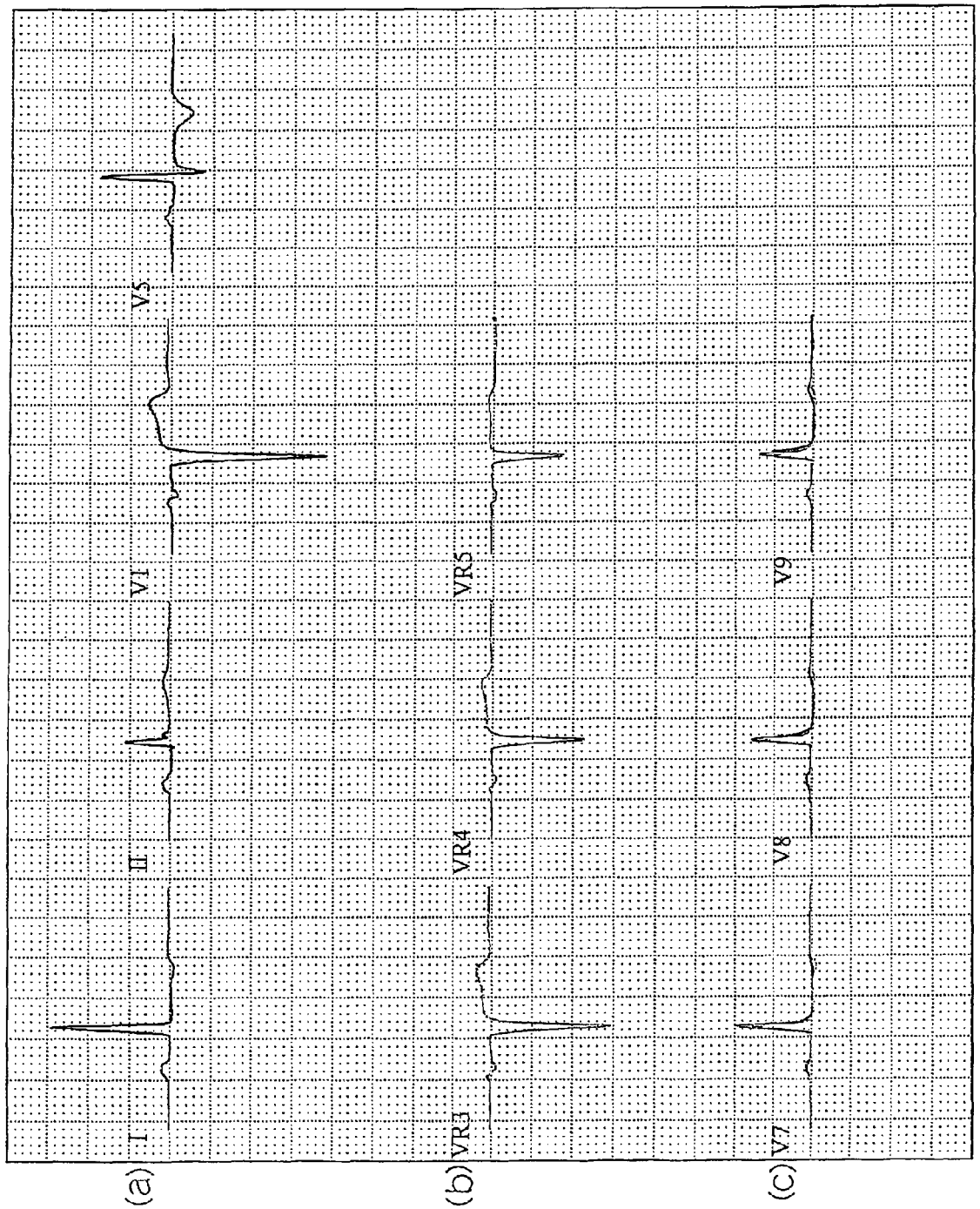
In FIG. 15, (a) shows measured waveforms of ECG signals (I, II, V1, and V5) of the standard 12-lead ECG, (b) calculated waveforms and measured waveforms of Leads V3R, V4R, and V5R of the extended lead ECG, and (c) calculated waveforms and measured waveforms of Leads V7, V8, and V9 of the extended lead ECG.
Figure 16:
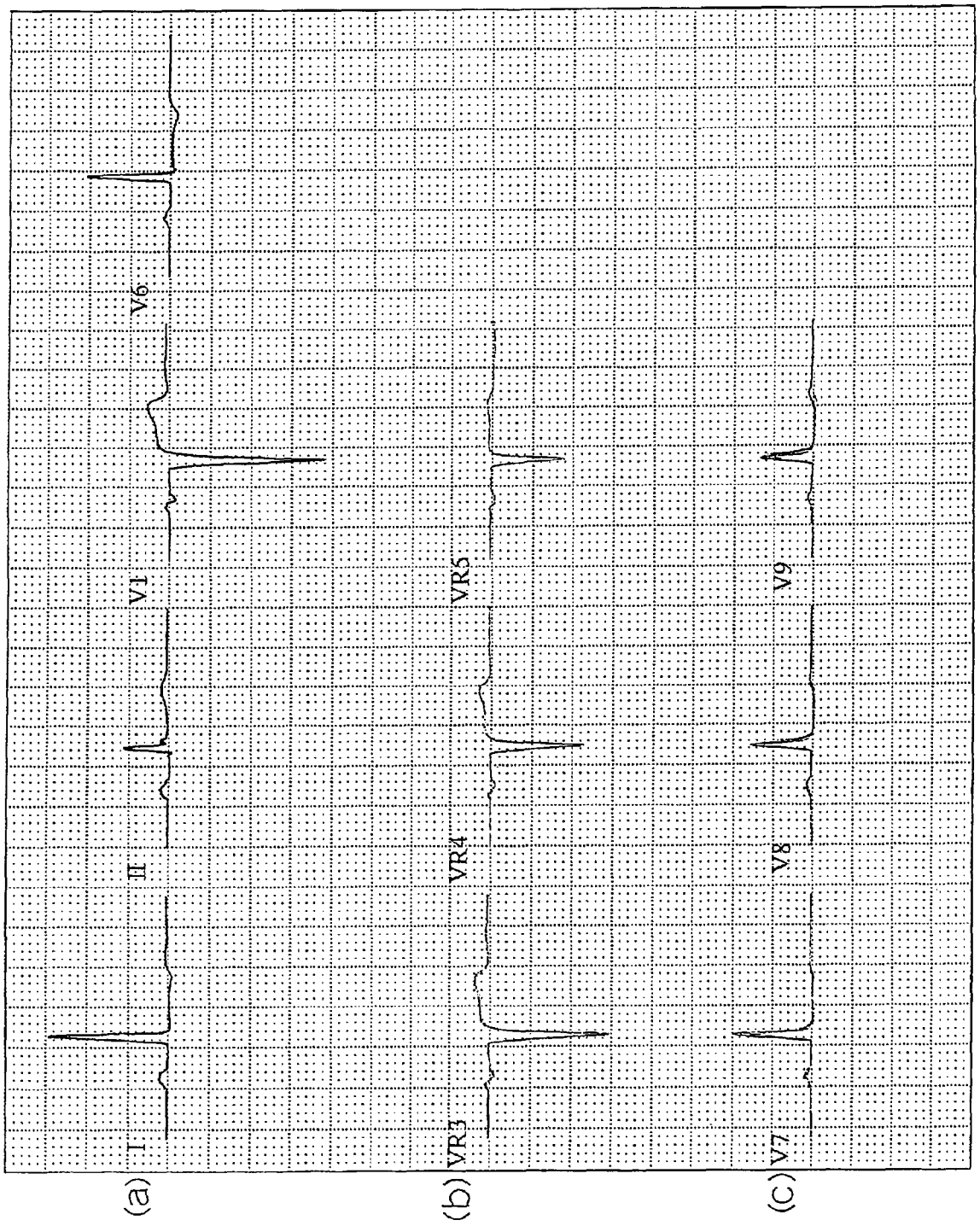
In FIG. 16, (a) shows measured waveforms of ECG signals (I, II, V1, and V6) of the standard 12-lead ECG, (b) calculated waveforms and measured waveforms of Leads V3R, V4R, and V5R of the extended lead ECG, and (c) calculated waveforms and measured waveforms of Leads V7, V8, and V9 of the extended lead ECG.
Figure 17:
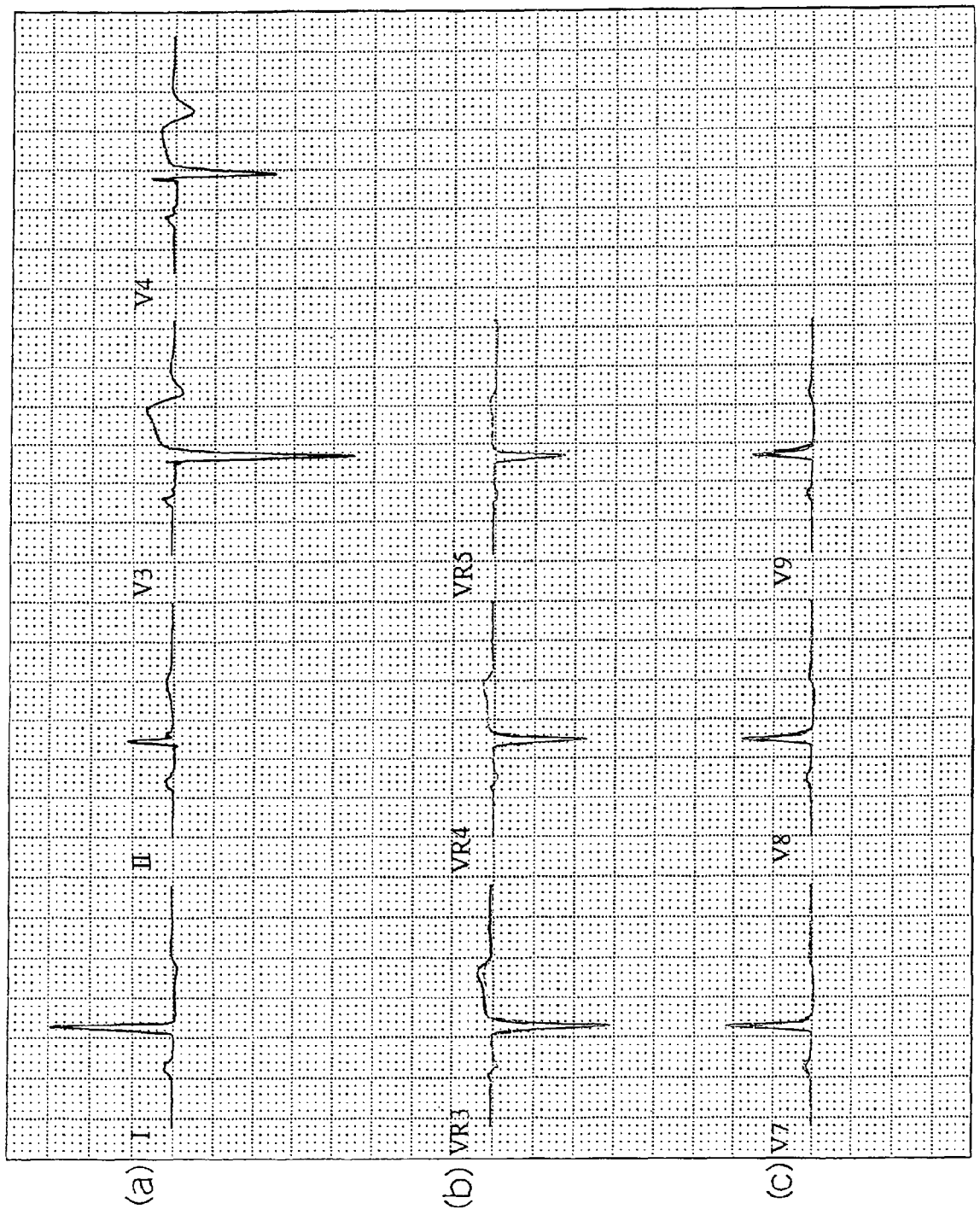
In FIG. 17, (a) shows measured waveforms of ECG signals (I, II, V3, and V4) of the standard 12-lead ECG, (b) calculated waveforms and measured waveforms of Leads V3R, V4R, and V5R of the extended lead ECG, and (c) calculated waveforms and measured waveforms of Leads V7, V8, and V9 of the extended lead ECG.
Figure 18:
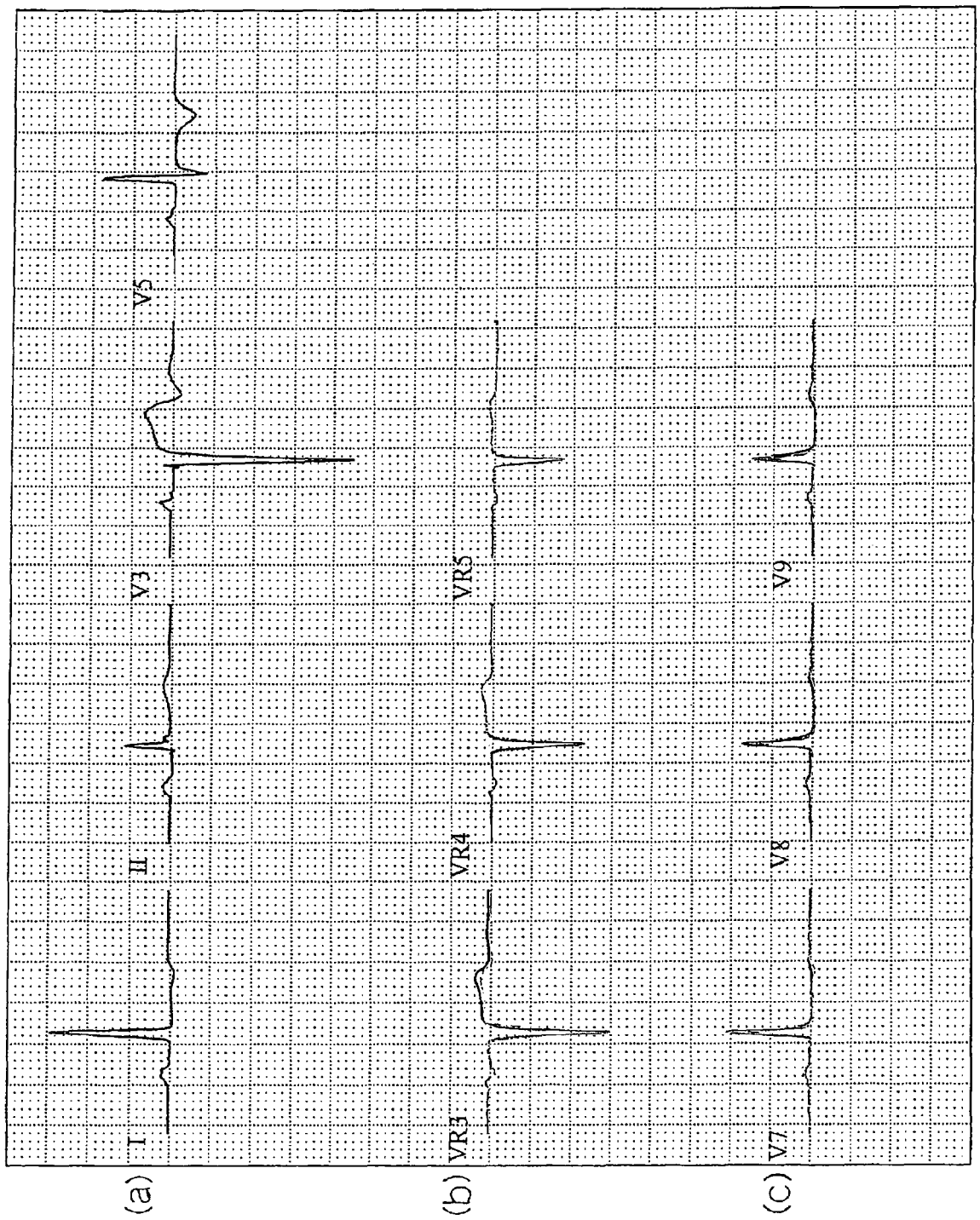
In FIG. 18, (a) shows measured waveforms of ECG signals (I, II, V3, and V5) of the standard 12-lead ECG, (b) calculated waveforms and measured waveforms of Leads V3R, V4R, and V5R of the extended lead ECG, and (c) calculated waveforms and measured waveforms of Leads V7, V8, and V9 of the extended lead ECG.

The system operation of the electrocardiograph with the extended lead function constructed in this manner will be described below with reference to the flowchart shown in FIG. 11.

In the electrocardiograph with the extended lead function, first, the potential detector 10A measures the ECG signals (I, II, V2, and V4) as the standard lead potentials of the standard 12-lead ECG of a patient (STEP-401). The ECG signals (I, II, V2, and V4) of the standard lead potentials thus measured are stored into the ECG signal memory 12A (STEP-402).

Next, the calculation transfer coefficients α preliminarily set in the memory 15A are fed to the extended lead ECG calculator 16A (STEP-403), and the ECG signals (I, II, V2, and V4) stored in the ECG signal memory 12A are also fed to the extended lead ECG calculator 16A, whereupon the extended lead ECG calculator 16A calculates the ECG signals (V7, V8, V9, $V_{3R}$, $V_{4R}$, and $V_{5R}$) of the extended lead ECG, based on the ECG signals (I, II, V2, and V4) and the transfer coefficients α (STEP-404). The arithmetic operation to calculate the ECG signals (V7, V8, V9, $V_{3R}$, $V_{4R}$, and $V_{5R}$) of the extended lead ECG by the extended lead ECG calculator 16A can be performed as follows, based on Eq (4-4).

$$\text{Lead } V_7: V_7 = \alpha_{7I}V_I + \alpha_{7II}V_{II} + \alpha_{7V2}V_{V2} + \alpha_{7V4}V_{V4} \quad (4\text{-}6)$$

$$\text{Lead } V_8: V_8 = \alpha_{8I}V_I + \alpha_{8II}V_{II} + \alpha_{8V2}V_{V2} + \alpha_{8V4}V_{V4} \quad (4\text{-}7)$$

$$\text{Lead } V_9: V_9 = \alpha_{9I}V_I + \alpha_{9II}V_{II} + \alpha_{9V2}V_{V2} + \alpha_{9V4}V_{V4} \quad (4\text{-}8)$$

$$\text{Lead } V_{3R}: V_{3R} = \alpha_{3RI}V_I + \alpha_{3RII}V_{II} + \alpha_{3RV2}V_{V2} + \alpha_{3RV4}V_{V4} \quad (4\text{-}9)$$

$$\text{Lead } V_{4R}: V_{4R} = \alpha_{4RI}V_I + \alpha_{4RII}V_{II} + \alpha_{4RV2}V_{V2} + \alpha_{4RV4}V_{V4} \quad (4\text{-}10)$$

$$\text{Lead } V_{5R}: V_{5R} = \alpha_{5RI}V_I + \alpha_{5RII}V_{II} + \alpha_{5RV2}V_{V2} + \alpha_{5RV4}V_{V4} \quad (4\text{-}11)$$

The ECG signals (I, II, V2, and V4) of the standard lead potentials stored in the ECG signal memory 12A are also fed to the standard 12-lead ECG calculator 14A, which performs the arithmetic operation to calculate the lead potentials (I, II, III, V1, V2, V3, V4, V5, V6, aVR, aVL, and aVF) of the standard 12-lead ECG (STEP-405). Here the lead potentials V1, V3, V5, and V6 are determined by the arithmetic operation based on the relationship among the potential vector, lead vector, and heart vector.

The ECG signals (V7, V8, V9, $V_{3R}$, $V_{4R}$, and $V_{5R}$) as the extended lead potentials of the extended lead ECG calculated by the extended lead ECG calculator 16A are subjected to waveform processing by the extended lead ECG waveform output device 18A and the result is fed to the display monitor 22A (STEP-406). The ECG signals (I, II, III, V1, V2, V3, V4, V5, V6, aVR, aVL, and aVF) as the lead potentials of the standard 12-lead ECG calculated by the standard 12-lead ECG calculator 14A are subjected to waveform processing by the standard 12-lead ECG waveform output device 20A (STEP-407) and the result is fed to the display monitor 22A (STEP-407). Furthermore, the extended lead ECG waveform output and the standard 12-lead ECG waveform output resulting from the waveform processing are simultaneously displayed on the display screen of the display monitor 22A (STEP-408).

FIGS. 12 to 18 show the waveform diagrams of the ECG signals (I, II, V1-V6) as the measured standard lead potentials of the standard 12 leads, and Leads V7, V8, V9 and Leads V3R, V4R, V5R as extended lead ECGs on the basis of the fourth embodiment. Similar output waveforms are also obtained by the third embodiment.

Specifically, FIG. 12(a) shows the waveforms of the ECG signals (I, II, V2, and V4) measured from a certain patient. FIG. 12(b) shows the waveforms of the respective leads V3R, V4R, and V5R as the extended lead ECG calculated from the ECG signals (I, II, V2, and V4), and the waveforms of the respective leads V3R, V4R, and V5R actually measured from the same patient (wherein the measured waveforms are indicated by thick solid lines and wherein portions overlapping with the waveforms calculated by the arithmetic operation are indicated by thin solid lines). FIG. 12(c) shows the waveforms of Leads V7, V8, and V9 (as indicated by thin solid lines) as the extended lead ECG calculated from the ECG signals (I, II, V2, and V4), and the waveforms of the respective leads V7, V8, and V9 actually measured from the same patient (wherein the measured waveforms are indicated by thick solid lines and wherein portions overlapping with the waveforms calculated by the arithmetic operation are indicated by thin solid lines). This result confirms that the waveforms of the extended lead ECG obtained by the calculation based on the fourth embodiment are extremely close to those of the extended lead ECG obtained by actual measurement.

FIG. 13(a) shows the waveforms of the ECG signals (I, II, V2, and V5) measured from another patient. FIG. 13(b) shows the waveforms of the respective leads V3R, V4R, and V5R as the extended lead ECG calculated from the ECG signals (I, II, V2, and V5), and the waveforms of the respective leads V3R, V4R, and V5R actually measured from the same patient (wherein the measured waveforms are indicated by thick solid lines and wherein portions overlapping with the waveforms calculated by the arithmetic operation are indicated by thin solid lines). FIG. 13(c) shows the waveforms of the respective leads V7, V8, and V9 (as indicated by thin solid lines) as the extended lead ECG calculated from the ECG signals (I, II, V2, and V5), and the waveforms of the respective leads V7, V8, and V9 actually measured from the same patient (wherein the measured waveforms are indicated by thick solid lines and wherein portions overlapping with the waveforms calculated by the arithmetic operation are indicated by thin solid lines). This result confirms that the waveforms of the extended lead ECG obtained by calculation based on the fourth embodiment are extremely close to the waveforms of the extended lead ECG obtained by actual measurement.

FIG. 14(a) shows the waveforms of the ECG signals (I, II, V2, and V6) measured from another patient. FIG. 14(b) shows the waveforms of the respective leads V3R, V4R, and V5R as the extended lead ECG calculated from the ECG signals (I, II, V2, and V6), and the waveforms of the respective leads V3R, V4R, and V5R actually measured from the same patient (wherein the measured waveforms are indicated by thick solid lines and wherein portions overlapping with the waveforms calculated by the arithmetic operation are indicated by thin solid lines). FIG. 14(c) shows the waveforms of the respective leads V7, V8, and V9 (as indicated by thin solid lines) as the extended lead ECG calculated from the ECG signals (I, II, V2, and V6), and the waveforms of the respective leads V7, V8, and V9 actually measured from the same patient (wherein the measured waveforms are indicated by thick solid lines and wherein portions overlapping with the waveforms calculated by the arithmetic operation are indicated by thin solid lines). This result confirms that the waveforms of the extended lead ECG obtained by calculation based on the fourth embodiment are extremely close to the waveforms of the extended lead ECG obtained by actual measurement.

FIG. 15(a) shows the waveforms of the ECG signals (I, II, V1, and V5) measured from another patient. FIG. 15(b) shows the waveforms of the respective leads V3R, V4R, and V5R as the extended lead ECG calculated from the ECG signals (I, II, V1, and V5), and the waveforms of the respective leads V3R, V4R, and V5R actually measured from the same patient (wherein the measured waveforms are indicated by thick solid lines and wherein portions overlapping with the waveforms calculated by the arithmetic operation are indicated by thin solid lines). FIG. 15(c) shows the waveforms of the respective leads V7, V8, and V9 (as indicated by thin solid lines) as the extended lead ECG calculated from the ECG signals (I, II, V1, and V5), and the waveforms of the respective leads V7, V8, and V9 actually measured from the same patient (wherein the measured waveforms are indicated by thick solid lines and wherein portions overlapping with the waveforms calculated by the arithmetic operation are indicated by thin solid lines). This result confirms that the waveforms of the extended lead ECG obtained by calculation based on the fourth embodiment are extremely close to the waveforms of the extended lead ECG obtained by actual measurement.

FIG. 16(a) shows the waveforms of the ECG signals (I, II, V1, and V6) measured from another patient. FIG. 16(b) shows the waveforms of the respective leads V3R, V4R, and V5R as the extended lead ECG calculated from the ECG signals (I, II, V1, and V6), and the waveforms of the respective leads V3R, V4R, and V5R actually measured from the same patient (wherein the measured waveforms are indicated by thick solid lines and wherein portions overlapping with the waveforms calculated by the arithmetic operation are indicated by thin solid lines). FIG. 16(c) shows the waveforms of the respective leads V7, V8, and V9 (as indicated by thin solid lines) as the extended lead ECG calculated from the ECG signals (I, II, V1, and V6), and the waveforms of the respective leads V7, V8, and V9 actually measured from the same patient (wherein the measured waveforms are indicated by thick solid lines and wherein portions overlapping with the waveforms calculated by the arithmetic operation are indicated by thin solid lines). This result confirms that the waveforms of the extended lead ECG obtained by calculation based on the fourth embodiment are extremely close to the waveforms of the extended lead ECG obtained by actual measurement.

FIG. 17(a) shows the waveforms of the ECG signals (I, II, V3, and V4) measured from another patient. FIG. 17(b) shows the waveforms of the respective leads V3R, V4R, and V5R as the extended lead ECG calculated from the ECG signals (I, II, V3, and V4), and the waveforms of the respective leads V3R, V4R, and V5R actually measured from the same patient (wherein the measured waveforms are indicated by thick solid lines and wherein portions overlapping with the waveforms calculated by the arithmetic operation are indicated by thin solid lines). FIG. 17(c) shows the waveforms of the respective leads V7, V8, and V9 (as indicated by thin solid lines) as the extended lead ECG calculated from the ECG signals (I, II, V3, and V4), and the waveforms of the respective leads V7, V8, and V9 actually measured from the same patient (wherein the measured waveforms are indicated by thick solid lines and wherein portions overlapping with the waveforms calculated by the arithmetic operation are indicated by thin solid lines). This result confirms that the waveforms of the extended lead ECG obtained by calculation based on the fourth embodiment are extremely close to the waveforms of the extended lead ECG obtained by actual measurement.

FIG. 18(a) shows the waveforms of the ECG signals (I, II, V3, and V5) measured from another patient. FIG. 18(b) shows the waveforms of the respective leads V3R, V4R, and V5R as the extended lead ECG calculated from the ECG signals (I, II, V3, and V5), and the waveforms of the respective leads V3R, V4R, and V5R actually measured from the same patient (wherein the measured waveforms are indicated by thick solid lines and wherein portions overlapping with the waveforms calculated by the arithmetic operation are indicated by thin solid lines). FIG. 18(c) shows the waveforms of the respective leads V7, V8, and V9 (as indicated by thin solid lines) as the extended lead ECG calculated from the ECG signals (I, II, V3, and V5), and the waveforms of the respective leads V7, V8, and V9 actually measured from the same patient (wherein the measured waveforms are indicated by thick solid lines and wherein portions overlapping with the waveforms calculated by the arithmetic operation are indicated by thin solid lines). This result confirms that the waveforms of the extended lead ECG obtained by calculation based on the fourth embodiment are extremely close to the waveforms of the extended lead ECG obtained by actual measurement.

It is noted that the present invention is by no means limited to the above embodiments. In the above embodiments, Leads I and II of the limb leads were selected and measured and the two leads of the chest leads were selected and measured out of the standard lead potentials of the standard 12-lead ECG (including the modified 12-lead ECG), and the extended lead ECG was determined from these leads. However, the present invention is not limited to such selection of leads, but the electrodes may be optionally selected; concerning the limb leads, it is also possible to select a combination of Leads I and III or a combination of Leads II and III. In this case, concerning the chest leads, it is possible to select an arbitrary combination from Leads V1-V6, of course. The present invention also allows the use of the chest leads among the Mason-Likar modified 12 leads to obtain the extended lead ECG of the modified 12-lead ECG in the case of an exercise load test or the like. The function of calculating the extended leads according to the present invention can also be added to the electrocardiographs in operation in hospital facilities and others, and can be marketed as an option for the electrocardiographs. Furthermore, this function of calculating the extended leads can also be added to biological information monitors for measuring other biological information in addition to the ECG. In addition, it is also possible to make a variety of design changes, without departing from the spirit of the present invention.

INDUSTRIAL APPLICABILITY

The present invention permits easy calculation and derivation of extended leads, without need for mounting electrodes for extended leads on a patient.

What is claimed is:

1. An electrocardiograph with an extended lead function comprising:
   a potential detector for measuring the limb leads I and II; and for measuring any one of the following combinations of chest leads, namely, chest leads V2 and V4, chest leads V2 and V5, chest leads V2 and V6, chest leads V1 and V5, chest leads V3 and V4, and chest leads V3 and V5, out of lead potentials of a standard 12-lead electrocardiogram (ECG); and
   extended lead potential calculating means for calculating an extended lead potential, based on the lead potentials of the 12-lead ECG measured by the potential detector, using the following equation (1):

$$V_i = \sum_j \alpha_{i,j} V_j; \quad (1)$$

wherein i is a lead number of an extended lead (V7, V8, V9, V3R, V4R, and V5R), and j is a lead number of one of the standard 12 leads (I, II, V1, V2, V3, V4, V5, and V6); and α is a transfer coefficient representing a relation among the leads, wherein said extended lead potential calculating means determines α in advance, by performing a least-squares computation based on measuring said limb leads I, II, and said one of said combinations of chest leads, and said extended leads, and substituting them into the following equation (2):

$$A = (V_j^T V_j)^{-1} V_j^T V_i; \quad (2)$$

wherein $A = \{\alpha_{i,j}\}$
$V_j = \{V_{s,j}\}$
$V_i = \{V_{i,s}\}$
T represents the transposition of a vector, and s represents a data sample;
wherein the potential detector and the calculating means use a subset of lead potentials less than the standard 12-lead ECG to calculate the extended lead potential.

2. An electrocardiograph with an extended lead function according to claim 1, further comprising:
   electrodes to be mounted on a body surface of a living body in order to obtain lead waveforms of a standard 12-lead ECG;
   standard 12-lead ECG waveform outputting means for performing waveform processing of the standard 12-lead ECG;
   extended lead ECG waveform outputting means for performing waveform processing of an extended lead ECG with input of the extended lead potential calculated by the extended lead potential calculating means; and
   a display monitor for simultaneously displaying on a screen, the ECG waveform outputs from the standard 12-lead ECG waveform outputting means and from the extended lead ECG waveform outputting means.

3. An electrocardiograph with an extended lead function according to claim 1, wherein
   said potential detector further measures the combination of chest leads V1 and V6; and
   said determination of said transfer coefficient α by said extended lead potential calculating means is further based on said combination of chest leads V1 and V6.

4. A method in an electrocardiograph with an extended lead function comprising the steps of:
   measuring potentials of the limb leads I and II; and measuring potentials of any one of the following combinations of chest leads, namely, chest leads V2 and V4, chest leads V2 and V5, chest leads V2 and V6, chest leads V1 and V5, chest leads V3 and V4, and chest leads V3 and V5, out of lead potentials of a standard 12-lead electrocardiogram (ECG); and
   calculating an extended lead potential, based on the measured lead potentials of the 12-lead ECG, using the following equation (1);

$$V_i = \sum_j \alpha_{i,j} V_j; \quad (1)$$

wherein i is a lead number of an extended lead (V7, V8, V9, V3R, V4R, and V5R), and j is a lead number of one of the standard 12 leads (I, II, V1, V2, V3, V4, V5, and V6); and α is a transfer coefficient representing a relation among the leads,
   further comprising the step of determining α in advance, by performing a least-squares computation based on measuring said limb leads I, II, and said one of said combinations of chest leads, and said extended leads, and substituting them into the following equation (2):

$$A = (V_j^T V_j)^{-1} V_j^T V_i; \quad (2)$$

wherein $A = \{\alpha_{i,j}\}$
$V_j = \{V_{s,j}\}$
$V_i = \{V_{i,s}\}$
T represents the transposition of a vector, and s represents a data sample;
wherein the measuring and the calculating use a subset of lead potentials less than the standard 12-lead ECG to calculate the extended lead potential.

5. A method in an electrocardiograph with an extended lead function according to claim 4, further comprising the steps of:
   measuring potentials of the combination of chest leads V1 and V6; and
   determining said transfer coefficient α based on said combination of chest leads V1 and V6.

6. An electrocardiograph with an extended lead function comprising:
   a potential detector configured to measure the limb leads I and II; and to measure chest leads of any one of the following combinations of chest leads, namely, chest leads V2 and V4, chest V2 and V5, chest leads V2 and V6, chest leads V1 and V5, chest leads V3 and V4, and chest leads V3 and V5, out of lead potentials of a standard 12-lead electrocardiogram (ECG); and
   an extended lead potential calculator configured to calculate an extended lead potential, based on the lead potentials of the 12-lead ECG measured by the potential detector, using the following equation (1):

$$V_i = \sum_j \alpha_{i,j} V_j; \quad (1)$$

wherein i is a lead number of an extended lead (V7, V8, V9, V3R, V4R, and V5R), and j is a lead number of one of the standard 12 leads (I, II, V1, V2, V3, V4, V5, and V6); and α is a transfer coefficient representing a relation among the leads, wherein said extended lead potential calculating means determines α in advance, by performing a least-squares computation based on measuring said limb leads I, II, and said one of said combinations of chest leads, and said extended leads, and substituting them into the following equation (2):

$$A = (V_j^T V_j)^{-1} V_j^T V_i \quad (2)$$

wherein $A = \{\alpha_{i,j}\}$
$V_j = \{V_{s,j}\}$
$V_i = \{V_{i,s}\}$
T represents the transposition of a vector, and s represents a data sample;

wherein the potential detector and the calculator use a subset of lead potentials less than the standard 12-lead ECG to calculate the extended lead potential.

7. An electrocardiograph with an extended lead function according to claim 6, wherein said potential detector is further configured for measuring the combination of chest leads V1 and V6; and said extended lead potential calculating means is further responsive to said combination of chest leads V1 and V6 for determining said transfer coefficient α.

* * * * *